US012030893B2

(12) United States Patent
Gibbs et al.

(10) Patent No.: US 12,030,893 B2
(45) Date of Patent: Jul. 9, 2024

(54) NEAR-INFRARED NERVE-SPARING BENZO[C]PHENOXAZINE FLUOROPHORES

(71) Applicant: OREGON HEALTH & SCIENCE UNIVERSITY, Portland, OR (US)

(72) Inventors: Summer L. Gibbs, West Linn, OR (US); Lei G. Wang, Portland, OR (US); Connor W. Barth, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 683 days.

(21) Appl. No.: 17/275,608

(22) PCT Filed: Sep. 11, 2019

(86) PCT No.: PCT/US2019/050680
§ 371 (c)(1),
(2) Date: Mar. 11, 2021

(87) PCT Pub. No.: WO2020/056046
PCT Pub. Date: Mar. 19, 2020

(65) Prior Publication Data
US 2022/0041619 A1 Feb. 10, 2022

Related U.S. Application Data

(60) Provisional application No. 62/729,932, filed on Sep. 11, 2018.

(51) Int. Cl.
*C07D 498/04* (2006.01)
*C09K 11/06* (2006.01)
*A61B 5/00* (2006.01)

(52) U.S. Cl.
CPC ............ *C07D 498/04* (2013.01); *C09K 11/06* (2013.01); *A61B 5/0071* (2013.01); *A61B 5/0075* (2013.01); *C09K 2211/1033* (2013.01)

(58) Field of Classification Search
CPC .................................................. C07D 498/04
See application file for complete search history.

(56) References Cited

U.S. PATENT DOCUMENTS

| 6,193,912 B1 | 2/2001 | Thieste et al. |
| 2016/0229840 A1 | 8/2016 | Shabat et al. |
| 2016/0347727 A1 | 12/2016 | Frangioni |

FOREIGN PATENT DOCUMENTS

| CN | 101257928 A | 9/2008 |
| CN | 103597039 A | 2/2014 |
| CN | 105073761 A | 11/2015 |
| WO | WO2015066296 A1 | 5/2015 |

OTHER PUBLICATIONS

Leitao, et al., "Benzo [a] phenoxazinium chlorides functionalized with chloride atoms and/or ester groups", 2015, 8 pages.
Pierce, et al., "Lasing Properties of Several Near-IR Dyes for a Nitrogen Laser-Pumped Dye Laser with an Optical Amplifier," IEEE Journal of Quantom Electronics, vol. QE-18, No. 7, 1982, pp. 1164-1170.
Park, et al., "Prototype Nerve-Specific Near-Infrared Fluorophores," Theranostics, vol. 4, No. 8, 2014, pp. 823-833.
PCT Search Report and Written Opinion for Application No. PCT/US19/50680, dated Nov. 27, 2019, 10 pages.
Canadian Office Action dated Dec. 12, 2023 for Canadian Application No. 3,111,574, a foreign counterpart to U.S. Appl. No. 17/275,608, 4 pages.
Anzalone et al., "A Common Diaryl Ether Intermediate for the Gram-Scale Assembly of Oxazine and Xanthen Fluorophores", Jan. 2013, Angew Chem Int Ed Engl., 52(2):650-654.
Chinese Office Action dated Nov. 3, 2022 for Chinese Application No. 201980066001.7, a foreign counterpart to U.S. Appl. No. 17/275,608, 6 pages.
Barth & Gibbs, "Direct Administration of Nerve-Specific Contrast to Improve Nerve Sparing Radical Prostatectomy," Theranostics, vol. 7, No. 3, 2017, pp. 573-593.
Belov, et al., "Rhodamine spiroamides for multicolor single-molecule switching fluorescent nanoscopy," Chemistry—A European Journal, vol. 15, No. 41, 2009, pp. 10762-10776.
Cotero, et al., "Intraoperative Fluorescence Imaging of Peripheral and Central Nerves Through a Myelin-Selective Contrast Agent," Molecular Imaging and Biology, vol. 14, 2012, pp. 708-717.
Gibbs, Summer L., "Near infrared fluorescence for image-guided surgery," Quantitative Imaging in Medicine and Surgery, vol. 2, No. 3, 2012, pp. 177-187.
Gibbs, et al., "Structure-activity relationship of nerve-highlighting fluorophores," PLoS One, vol. 8, No. 9, 2013, 12 pages.
Gibbs-Strauss, et al., "Molecular Imaging Agents Specific for the Annulus Fibrosus of the Intervertebral Disk," Molecular Imaging, vol. 9, No. 3, 2010, pp. 128-140.
Gibbs-Strauss, et al., "Nerve-highlighting fluorescent contrast agents for image-guided surgery," Molecular Imaging, vol. 10, No. 2, 2011, pp. 91-101.
Klapares & Buchwald, "Copper-Catalyzed Halogen Exchange in Aryl Halides: An Aromatic Finkelstein Reaction," Journal of the American Chemical Society, vol. 124, No. 50, 2002, pp. 14844-14845.
Maiti & Buchwald, "Orthogonal Cu- and Pd-Based Catalyst Systems for the O- and N-Arylation of Aminophenols," Journal of the American Chemical Society, vol. 131, No. 47, 2009, pp. 17423-17429.
Meyers, et al., "Lighting up the Senses: FM1-43 Loading of Sensory Cells through Nonselective Ion Channels," Journal of Neuroscience, vol. 23, No. 10, 2003, pp. 4054-4065.
Stankoff, et al., "Imaging of CNS myelin by positron-emission tomography," PNAS USA, vol. 103, No. 24, 2006, pp. 9304-9309.

(Continued)

*Primary Examiner* — Yong S. Chong
(74) *Attorney, Agent, or Firm* — Lee & Hayes, P.C.

(57) ABSTRACT

Provided are near-infrared nerve-sparing fluorescent compounds, compositions comprising them, and methods of their use in medical procedures.

20 Claims, 8 Drawing Sheets

(56) References Cited

OTHER PUBLICATIONS

Vahrmeijer, et al., "Image-guided cancer surgery using near-infrared fluorescence," Nature Reviews Clinical Oncology, vol. 10, No. 9, 2013, pp. 507-518.

Wang, et al., "In situ fluorescence imaging of myelination," Journal of Histochemistry & Cytochemistry, vol. 58, No. 7, 2010, pp. 611-621.

Wang, et al., "Longitudinal Near-Infrared Imaging of Myelination," Journal of Neuroscience, vol. 31, No. 7, 2011, pp. 2382-2390.

Whitney, et al., "Fluorescent peptides highlight peripheral nerves during surgery in mice," Nature Biotechnology, vol. 29, 2011, pp. 352-356.

Wu, et al., "Molecular probes for imaging myelinated white matter in CNS," Journal of Medicinal Chemistry, vol. 51, No. 21, 2008, pp. 6682-6688.

NEAR-INFRARED NERVE-SPARING BENZO[C]PHENOXAZINE FLUOROPHORES

CROSS REFERENCE TO RELATED APPLICATIONS

This is the U.S. National Phase of PCT/US2019/050680, filed Sep. 11, 2019, which claims priority to and the benefit of the earlier filing date of U.S. Provisional Application No. 62/729,932, filed Sep. 11, 2018, both of which are incorporated herein by reference in their entireties as if fully set forth herein.

STATEMENT REGARDING FEDERALLY SPONSORED RESEARCH OR DEVELOPMENT

This invention was made with government support under R01 EB021362 awarded by the National Institutes of Health. The government has certain rights in the invention.

This invention concerns near-infrared nerve-sparing fluorescent compounds, compositions comprising them, and methods of their use in medical procedures.

BACKGROUND OF THE INVENTION

Accidental nerve transection or injury is a major morbidity associated with many surgical interventions, resulting in persistent postsurgical numbness, chronic pain, and/or paralysis. Nerve sparing can be a difficult task due to patient-to-patient variability and the difficulty of nerve visualization in the operating room. Currently, nerve detection in the operating room is largely completed through electromyographical monitoring, ultrasound or direct visualization under white light. Fluorescence-guided surgery to aid in the precise visualization of vital nerve structures in real time could greatly improve patient outcomes. However, no clinically approved nerve-specific contrast agent exists. Contrast agents that fall within the near-infrared (NIR) window (650-900 nm) are particularly attractive for fluorescence-guided surgery because absorbance, scatter and autofluorescence are all at local minima, making tissue light penetration maximal in this range. To date, a NIR nerve-specific fluorophore does not exist, where Oxazine 4 has the longest emission wavelength (635 nm maximum) among the nerve-specific fluorophores that have been reported to highlight peripheral nerves. This is a particularly challenging problem because nerve-specific contrast agents must have a relatively low molecular weight in order to cross the blood-nerve barrier. Complicating this requirement is the fact that NIR fluorophores must have a sufficient degree of conjugation to reach NIR wavelengths, by definition increasing their molecular weight. There remains a need for NIR nerve-specific contrast agents that improve nerve visualization for diagnostic procedures and use during fluorescence-guided surgery. Herein we report our efforts to synthesize a focused library of systematically-modified NIR fluorophores to define the factors that modulate a fluorophore's nerve specificity.

SUMMARY OF THE INVENTION

Provided is a compound of Formula I:

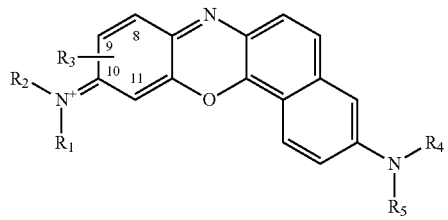

Formula I wherein $R_1$ is selected from hydrogen and $C_1$-$C_3$ alkyl;

$R_2$ is selected from hydrogen and $C_1$-$C_3$ alkyl;

$R_3$ is selected from the group of hydrogen, halogen, and $C_1$-$C_3$ alkyl;

or, when $R_3$ is bound to the 9-position carbon of the 10H-benzo[c]phenoxazine core, $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents; and $R_4$ and $R_5$ are each independently selected from hydrogen and $C_1$-$C_3$ alkyl.

Further provided are pharmaceutically acceptable compositions comprising an effective amount of a compound of Formula I, as well as methods for using such formulations and compounds in imaging techniques.

DETAILED DESCRIPTION OF THE INVENTION

Figure 1:
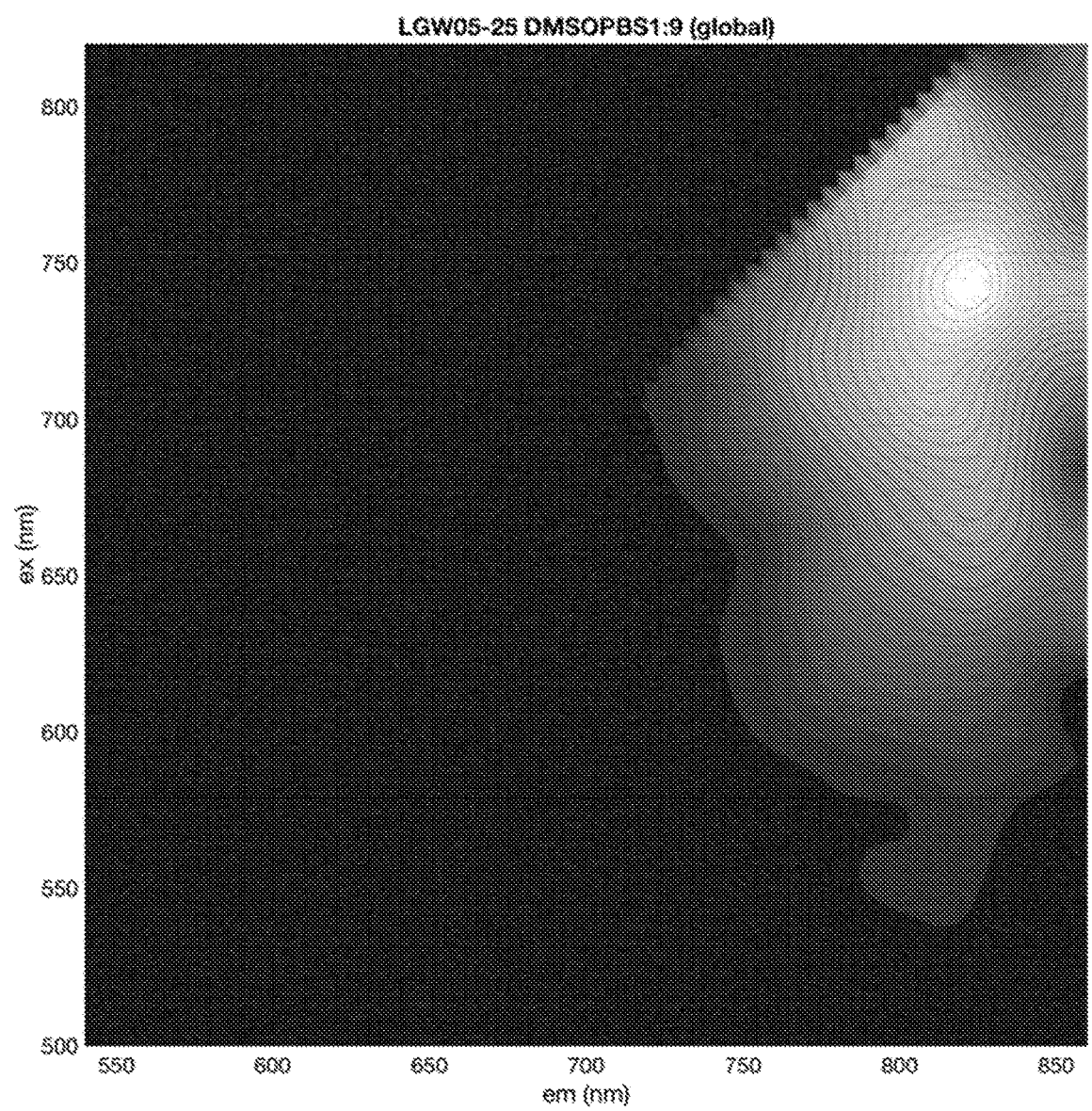
FIG. 1 represents Excitation Emission Matrices (EEMs) of compound LGW05-25 in phosphate buffered saline solution containing 10% DMSO.
Figure 2A:
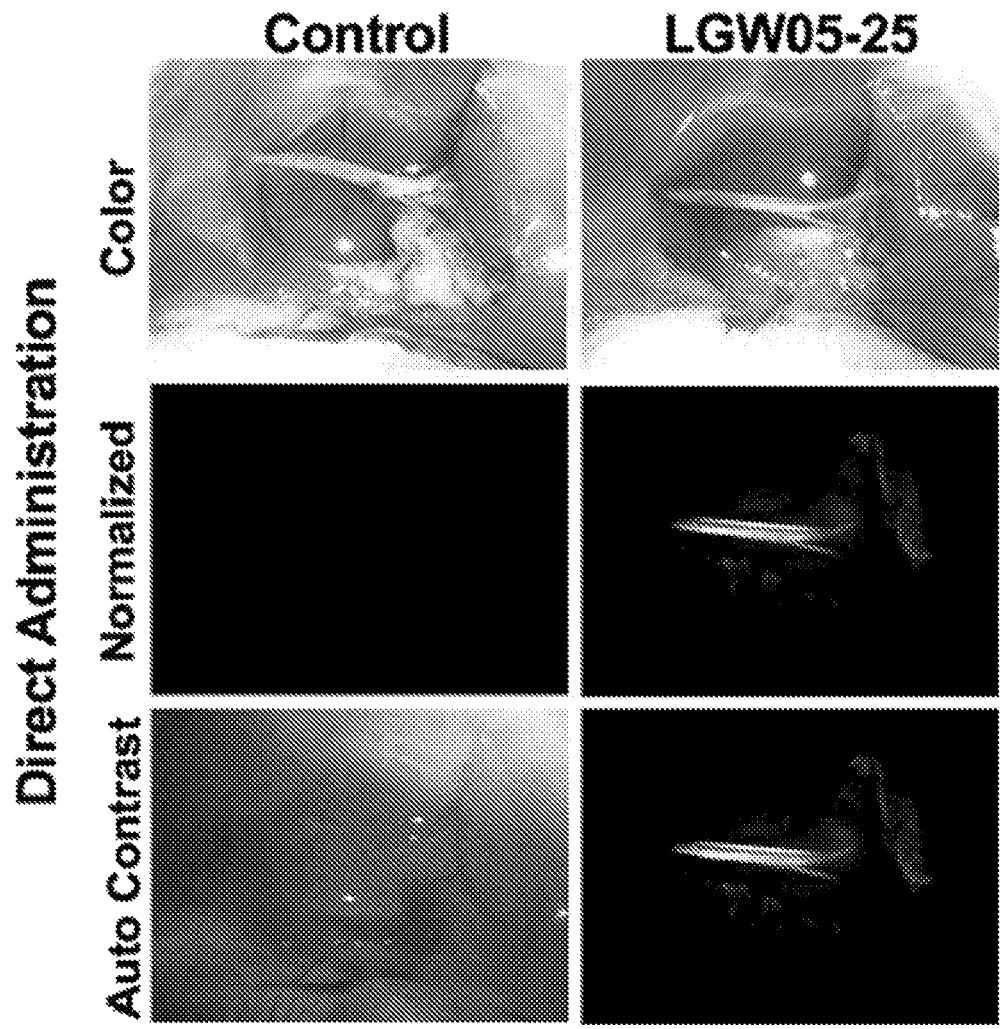
FIGS. 2A and 2B depict the contrast represented by direct administration (2A) and systemic direct administration (2B) of compound LG05-25.
Figure 2B:
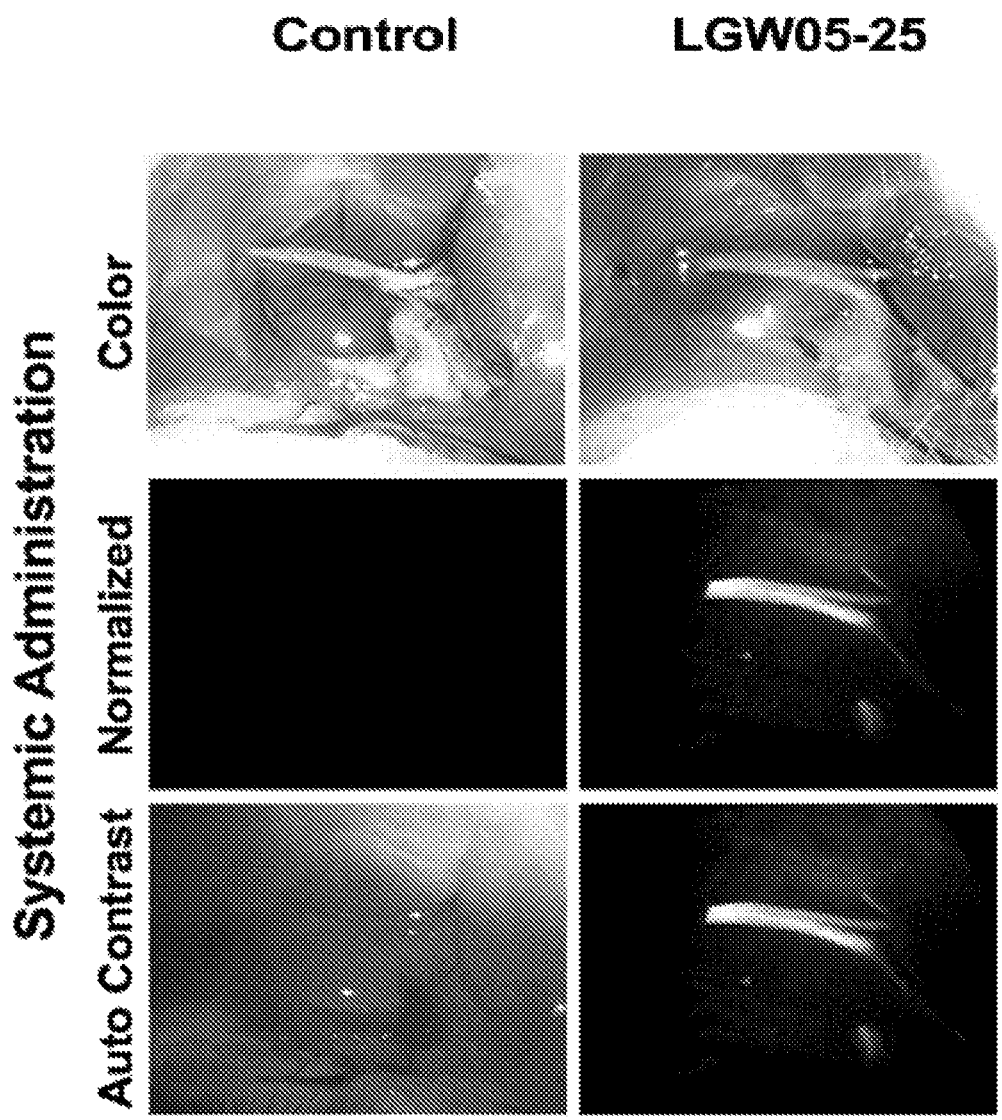

Provided herein are also embodiments comprising a compound of Formula Ia, Formula Ib, and Formula Ic, or a pharmaceutically acceptable salt thereof, as shown below:

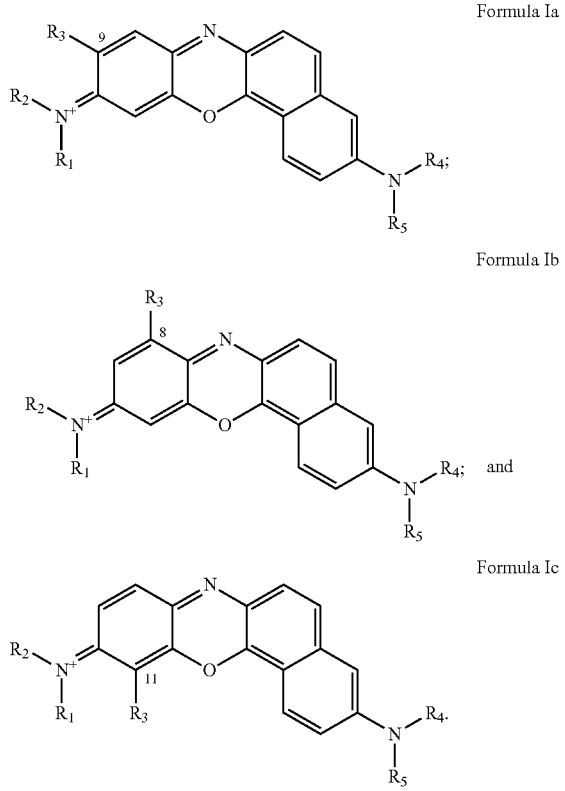

Formula Ia

Formula Ib

Formula Ic

Other separate embodiments provide a compound of Formula I, Formula Ia, Formula Ib, and Formula Ic, wherein, in each instance, $R_1$ is hydrogen; $R_2$ is $C_1$-$C_3$ alkyl; $R_3$ is selected from the group of hydrogen, halogen, and $C_1$-$C_3$ alkyl; and $R_4$ and $R_5$ are each independently selected from hydrogen and $C_1$-$C_3$ alkyl.

Other separate embodiments provide a compound of Formula I, Formula Ia, Formula Ib, and Formula Ic, wherein, in each instance, $R_1$ is hydrogen; $R_2$ is $C_1$-$C_3$ alkyl; $R_3$ is selected from the group of hydrogen, F, Cl, and $C_1$-$C_3$ alkyl; and $R_4$ and $R_5$ are each independently selected from hydrogen and $C_1$-$C_3$ alkyl.

Other separate embodiments provide a compound of Formula I, Formula Ia, Formula Ib, and Formula Ic, wherein, in each instance, $R_1$ is hydrogen; $R_2$ is $C_1$-$C_3$ alkyl; $R_3$ is selected from the group of hydrogen, F, Cl, and $C_1$-$C_3$ alkyl; and $R_4$ and $R_5$ are each independently $C_1$-$C_3$ alkyl.

Other separate embodiments provide a compound of Formula I, Formula Ia, Formula Ib, and Formula Ic, wherein, in each instance, $R_1$ is hydrogen; $R_2$ is $C_1$-$C_2$ alkyl; $R_3$ is selected from the group of hydrogen, F, Cl, and $C_1$-$C_2$ alkyl; and $R_4$ and $R_5$ are each independently $C_1$-$C_2$ alkyl.

Other separate embodiments provide a compound of Formula I, Formula Ia, Formula Ib, and Formula Ic, wherein, in each instance, $R_1$ is hydrogen; $R_2$ is $C_1$-$C_2$ alkyl; $R_3$ is $C_1$-$C_2$ alkyl; and $R_4$ and $R_5$ are each independently $C_1$-$C_2$ alkyl.

Other separate embodiments provide a compound of Formula I, Formula Ia, Formula Ib, and Formula Ic, wherein, in each instance, $R_1$ is hydrogen; $R_2$ is ethyl; $R_3$ is $C_1$-$C_2$ alkyl; and $R_4$ and $R_5$ are each ethyl.

Another embodiment comprises a compound of Formula Ia
wherein $R_1$ is selected from hydrogen and $C_1$-$C_3$ alkyl;
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents; and
$R_4$ and $R_5$ are each independently selected from hydrogen and $C_1$-$C_3$ alkyl.

A further embodiment comprises a compound of Formula Ia
wherein $R_1$ is selected from hydrogen and $C_1$-$C_3$ alkyl;
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_2$ alkyl substituents; and
$R_4$ and $R_5$ are each independently selected from hydrogen and $C_1$-$C_2$ alkyl.

Another embodiment comprises a compound of Formula II:

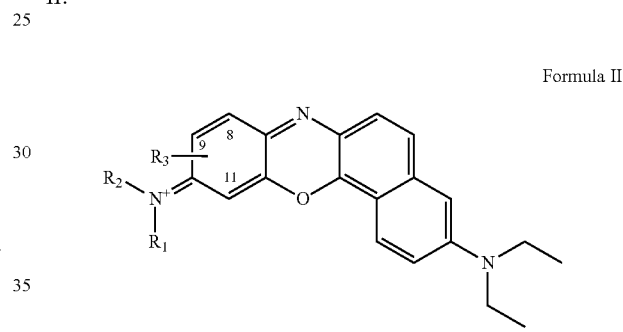

Formula II wherein $R_1$ is selected from hydrogen and $C_1$-$C_3$ alkyl;
$R_2$ is selected from hydrogen and $C_1$-$C_3$ alkyl;
$R_3$ is selected from the group of hydrogen, halogen, and $C_1$-$C_3$ alkyl;
or, when $R_3$ is bound to the 9-position carbon of the 10H-benzo[c]phenoxazine core, $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents.

In separate embodiments are also provided a compound selected from Formula IIa, Formula IIb, and Formula IIc, wherein in each instance $R_1$, $R_2$, and $R_3$ are as defined above for Formula II:

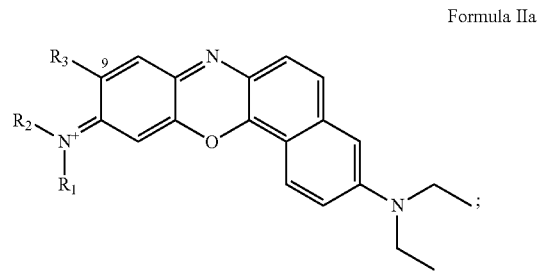

Formula IIa

Formula IIb

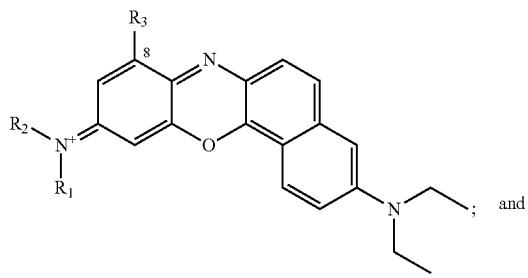

Formula IIc

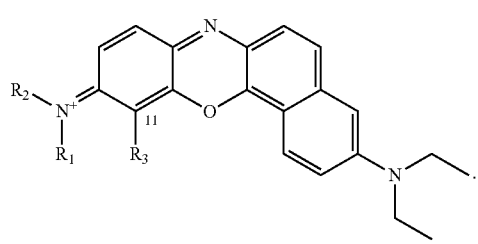

Other separate embodiments provide a compound of Formula II, Formula IIa, Formula IIb, and Formula IIc, wherein, in each instance, $R_1$ is hydrogen; $R_2$ is $C_1$-$C_3$ alkyl; and $R_3$ is selected from the group of hydrogen, halogen, and $C_1$-$C_3$ alkyl.

Other separate embodiments provide a compound of Formula II, Formula IIa, Formula IIb, and Formula IIc, wherein, in each instance, $R_1$ is hydrogen; $R_2$ is $C_1$-$C_3$ alkyl; and $R_3$ is selected from the group of hydrogen, F, Cl, and $C_1$-$C_3$ alkyl.

Other separate embodiments provide a compound of Formula II, Formula IIa, Formula IIb, and Formula IIc, wherein, in each instance, $R_1$ is hydrogen; $R_2$ is $C_1$-$C_2$ alkyl; and $R_3$ is selected from the group of hydrogen, F, Cl, and $C_1$-$C_2$ alkyl.

Another embodiment comprises a compound of Formula IIa, wherein $R_1$ is selected from hydrogen and $C_1$-$C_3$ alkyl; and $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents.

Still another embodiment comprises a compound of Formula IIa, wherein $R_1$ is selected from hydrogen and $C_1$-$C_2$ alkyl; and $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_2$ alkyl substituents.

Another embodiment provides a compound of Formula III:

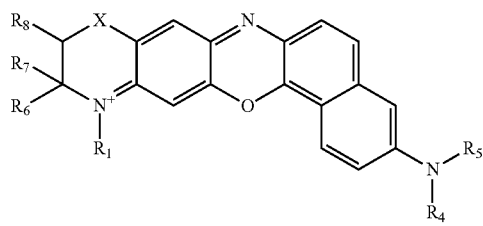

Formula III wherein $R_1$ is selected from hydrogen and $C_1$-$C_3$ alkyl;
$R_4$ and $R_5$ are each independently selected from hydrogen and $C_1$-$C_3$ alkyl;
$R_6$, $R_7$, and $R_8$ are each independently hydrogen or $C_1$-$C_3$ alkyl;
X is selected from oxygen and carbon, with carbon atom being optionally substituted by $C_1$-$C_3$ alkyl.

Also provided is a compound of Formula III, wherein $R_1$ is selected from hydrogen and $C_1$-$C_2$ alkyl;
$R_4$ and $R_5$ are each independently selected from hydrogen and $C_1$-$C_2$ alkyl;
$R_6$, $R_7$, and $R_8$ are each independently hydrogen or $C_1$-$C_2$ alkyl; and
X is selected from oxygen and carbon, with carbon atom being optionally substituted by $C_1$-$C_2$ alkyl.

Further provided is a compound of Formula III, wherein $R_1$ is selected from hydrogen and —$CH_3$;
$R_4$ and $R_5$ are each independently selected from hydrogen and $C_1$-$C_2$ alkyl;
$R_6$, $R_7$, and $R_8$ are each independently hydrogen or —$CH_3$; and
X is selected from oxygen and carbon, with carbon atom being optionally substituted by —$CH_3$.

Within each of the embodiments herein for a compound of Formula III, there is a further embodiment in which $R_1$, $R_6$, $R_7$, $R_8$ and X are as defined for the embodiment in question and $R_4$ and $R_5$ are each ethyl.

A further embodiment provides a compound of Formula IV:

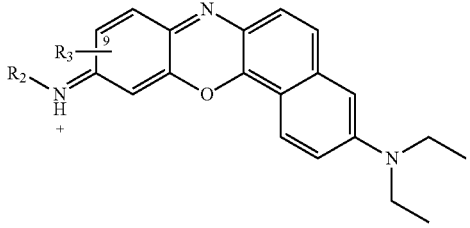

Formula IV wherein $R_3$ is methyl and $R_2$ is ethyl;
or, when $R_3$ is bound to the 9-position carbon of the 10H-benzo[c]phenoxazine core, $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a five-membered fused ring substituted by 0, 1, 2, or 3 $C_1$-$C_3$ alkyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a five-membered fused ring substituted by 0, 1, 2, or 3 $C_1$-$C_2$ alkyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a five-membered fused ring substituted by 0, 1, 2, or 3 methyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a six-membered fused ring substituted by 0, 1, 2, or 3 $C_1$-$C_3$ alkyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a six-membered fused ring substituted by 0, 1, 2, or 3 $C_1$-$C_2$ alkyl substituents.

Another embodiment comprises a compound of Formula IV wherein $R_3$ is methyl and $R_2$ is ethyl;

or, when $R_3$ is bound to the 9-position carbon of the 10H-benzo[c]phenoxazine core, $R_2$ and $R_3$, together with the carbon atoms to which they are bonded, form a six-membered fused ring substituted by 0, 1, 2, or 3 methyl substituents.

Examples of compounds within the groups described herein include those selected from the group of:

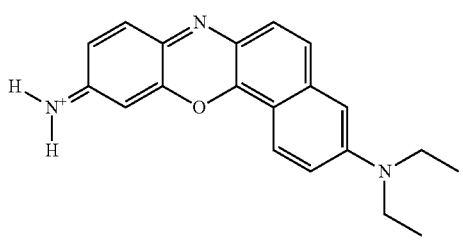 [SMILES: CCN(CC)c1ccc2c(ccc3nc4ccc(=[NH2+])cc-4oc32)c1]

3-(diethylamino)-10H-benzo[c]phenoxazin-10-iminium

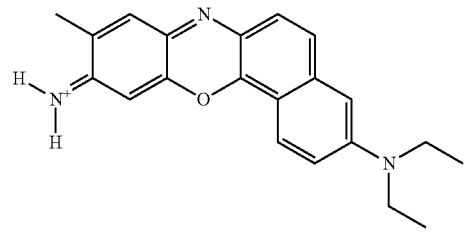 [SMILES: CCN(CC)c1ccc2c(ccc3nc4cc(C)c(=[NH2+])cc-4oc32)c1]

3-(diethylamino)-9-methyl-10H-benzo[c]phenoxazin-10-iminium

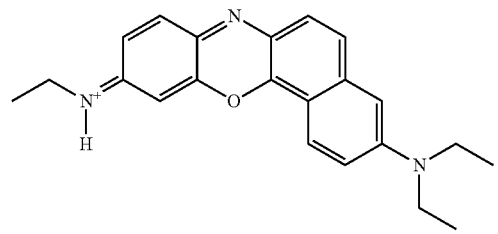 [SMILES: CC/[NH+]=c1\ccc2nc3ccc4cc(N(CC)CC)ccc4c3oc-2c1]

(E)-N-(3-(diethylamino)-10H-benzo[c]phenoxazin-10-ylidene)ethanaminium

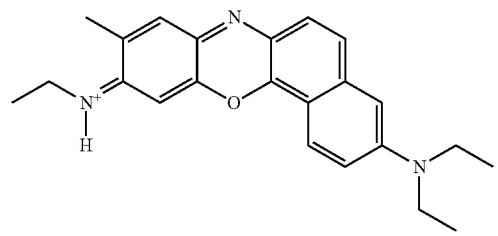

(Z)—N-(3-(diethylamino)-9-methyl-10H-benzo[c]phenoxazin-10-ylidene)ethanaminium

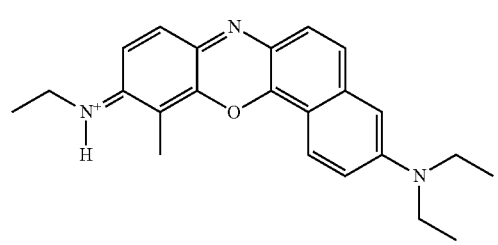 [SMILES: CC/[NH+]=c1\ccc2nc3ccc4cc(N(CC)CC)ccc4c3oc-2c1C]

| 9 | 10 |
|---|---|
| (E)-N-(3-(diethylamino)-11-methyl-10H-benzo[c]phenoxazin-10-ylidene)ethanaminium | 3-(diethylamino)-10,11-dihydrobenzo[h][1,4]oxazino[2,3-b]phenoxazin-12-ium |

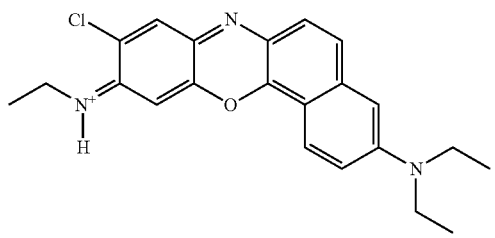 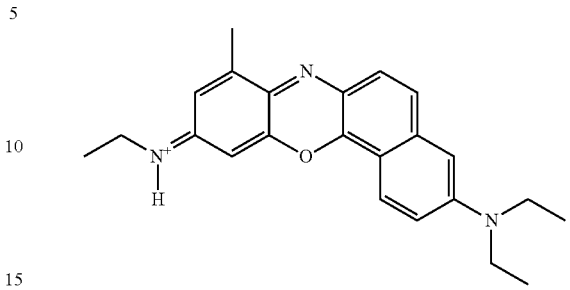

(Z)—N-(9-chloro-3-(diethylamino)-10H-benzo[c]phenoxazin-10-ylidene)ethanaminium (E)-N-(3-(diethylamino)-8-methyl-10H-benzo[c]phenoxazin-10-ylidene)ethanaminium

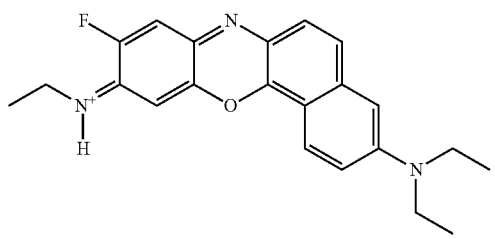 [SMILES: CC/[NH+]=c1/cc2oc3c(ccc4cc(N(CC)CC)ccc43)nc-2cc1F] 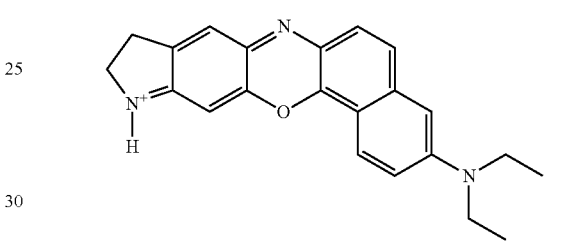

(Z)—N-(3-(diethylamino)-9-fluoro-10H-benzo[c]phenoxazin-10-ylidene)ethanaminium 3-(diethylamino)-9,10-dihydrobenzo[h]pyrrolo[3,2-b]phenoxazin-11-ium

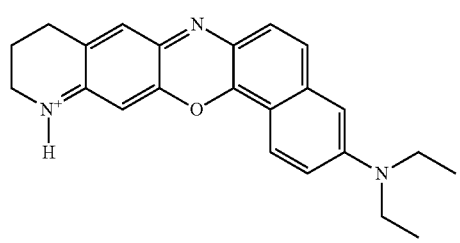 [SMILES: CCN(CC)c1ccc2c3c(ccc2c1)N=c1cc2c(cc1O3)=[NH+]CCC2] 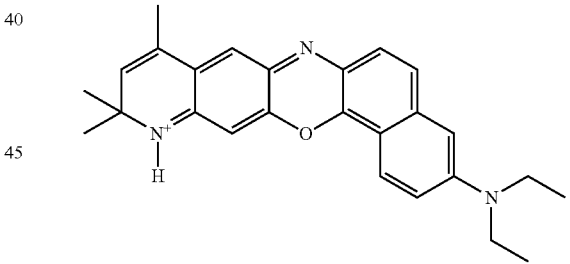

3-(diethylamino)-10,11-dihydro-9H-benzo[h]pyrido[3,2-b]phenoxazin-12-ium 3-(diethylamino)-9,11,11-trimethyl-11H-benzo[h]pyrido[3,2-b]phenoxazin-12-ium

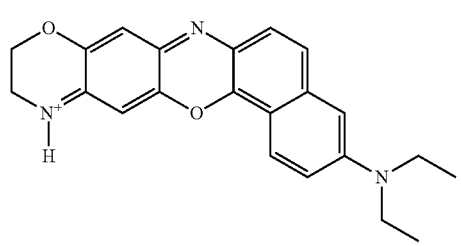 [SMILES: CCN(CC)c1ccc2c3c(ccc2c1)N=c1cc2c(cc1O3)=[NH+]CCO2] 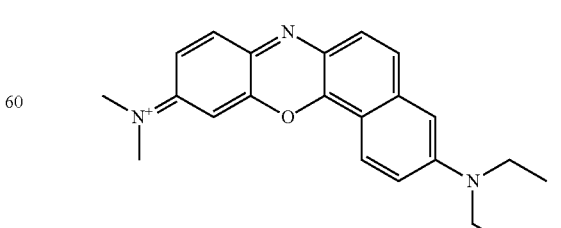

N-(3-(diethylamino)-10H-benzo[c]phenoxazin-10-ylidene)-N-methylmethanaminium; and

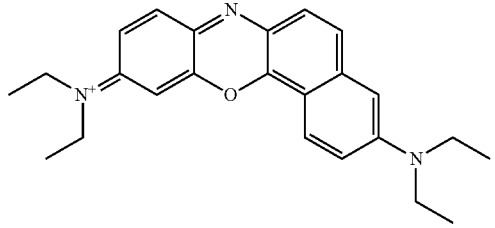 [SMILES: CCN(CC)c1ccc2c(ccc3nc4ccc(=[N+](CC)CC)cc-4oc32)c1]

N-(3-(diethylamino)-10H-benzo[c]phenoxazin-10-ylidene)-N-ethylethanaminium

Also provided herein are pharmaceutical or medical compositions comprising one or more fluorophore compound(s) described herein and a pharmaceutically or medically acceptable carrier or excipient. In some embodiments the composition is intended for direct/topical administration. Direct administration refers to an application of the compound or composition in question directly to a tissue or organ of interest, such as by irrigation, misting, spraying, swabbing, wiping, brushing, or other means of direct application. Systemic administration refers to administration of a compound or composition such that an entire system, organ, or tissue of interest receives compound dispersion sufficient for imaging or other medical purposes. Systemic administration includes parenteral administration, such as intravenous, intramuscular, or subcutaneous administrations by injection, infusion, or other means.

Suitable pharmaceutically-acceptable nonaqueous solvents that may be used as carriers or excipients with the present compounds include the following (as well as mixtures thereof): alcohols (these include, for example, σ-glycerol formal, β-glycerol formal, 1,3-butyleneglycol; aliphatic or aromatic alcohols such as methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol); fatty acid esters of fatty alcohols (polyalkylene glycols, such as polypropylene glycol and polyethylene glycol), sorbitan, sucrose, and cholesterol; amides such as dimethylacetamide (DMA), benzyl benzoate DMA, dimethylformamide, N-hydroxyethyO-lactamide, N,N-dimethylacetamide-amides, 2-pyrrolidinone, 1-methyl-2-pyrrolidinone, and polyvinylpyrrolidone; acetate esters, such as monoacetin, diacetin, and triacetin; aliphatic and aromatic esters, such as ethyl caprylate or octanoate, alkyl oleate, benzyl benzoate, or benzyl acetate; dimethylsulfoxide (DMSO); esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., Poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATEs 20, 40, 60, and 80, polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters); ethers such as diethyl ether, tetrahydrofuran, dimethyl isosorbide, diethylene glycol monoethyl ether), and glycofurol (tetrahydrofurfuranyl alcohol polyethylene glycol ether); ketones such as acetone, methyl ethyl ketone, methyl isobutyl ketone; hydrocarbons such as benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide; oils such as mineral oils, vegetable oils, glycerides, animal oils, oleic oils, alkyl, alkenyl, or aryl halides, monoethanolamine; petroleum benzin; trolamine; omega-3 polyunsaturated fatty acids such as alpha-linolenic acid, eicosapentaenoic acid, docosapentaenoic acid, or docosahexaenoic acid; polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate. Other pharmaceutically acceptable solvents for use in the invention are well known to those of ordinary skill in the art.

Additional components can cryoprotective agents; agents for preventing reprecipitation of the dithienopyrrole compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); and diluents (e.g., water, saline, electrolyte solutions, etc.).

One embodiment provides a composition comprising at least one fluorescent compound as described herein, such as a compound of Formula I, and dimethyl sulfoxide (DMSO).

Definitions

The terms "administer," "administering", "administration," and the like, as used herein, refer to methods used to enable delivery of agents or compositions disclosed herein to the desired site of action, such as a site to be medically imaged. These methods include, but are not limited to parenteral injection (e.g., intravenous, subcutaneous, intraperitoneal, intramuscular, intravascular, intrathecal, intravitreal, infusion, or local). In some embodiments the administration is topical. Administration techniques that are optionally employed with the agents and methods described herein, include e.g., as discussed in Goodman and Gilman, The Pharmacological Basis of Therapeutics, current ed.;

Pergamon; and Remington's, Pharmaceutical Sciences (current edition), Mack Publishing Co., Easton, Pa.

The terms "effective amount" or "medically effective amount" or like terms refers to an amount of a compound or composition as described herein to cover a target area sufficiently to complete binding to one or more nerves such that they may be identified through relevant imaging techniques, particularly near-infrared imaging techniques.

The term "imaging" herein refers to the use of fluorescent compounds in conventional medical imaging techniques including, but not limited to, those related to fluorescence image-guided surgery (including minimally invasive laparoscopy or endoscopy techniques), computer-assisted surgery or surgical navigation, radiosurgery or radiation therapy, interventional radiology, fluorescence microscopy, and laser-confocal microscopy. These techniques may include near infrared wavelengths from about 650 nm to 900 nm.

The term "label" refers to a molecule that facilitates the visualization and/or detection of a targeting molecule disclosed herein. In some embodiments, the label is a fluorescent moiety.

As used herein, the term "neuron" means an electrically excitable cell that processes and transmits information by electrical and chemical signaling. Neurons possess a cell body (i.e., the soma), dendrites, and an axon. Neurons are electrically excitable, maintaining voltage gradients across their membranes by ion pumps, which combine with ion channels embedded in the membrane to generate intracellular-versus-extracellular concentration differences of ions (e.g., sodium, potassium, chloride, and calcium). A neuron may or may not include a myelin sheath. The term "neuron" is intended to include any tissues (e.g., the sinoatrial node or atrioventricular node) or structures associated therewith (e.g., neuromuscular junctions).

The term "nerve" means a bundle of neural axons. Within a nerve, each axon is surrounded by a layer of connective tissue called the endoneurium. The axons are bundled together into groups called fascicles, and each fascicle is wrapped in a layer of connective tissue called the perineurium. The entire nerve is wrapped in a layer of connective tissue called the epineurium. The term "nerve" is intended to include any tissues (e.g., the sinoatrial node or the atriventricular node) or structures associated therewith (e.g., neuromuscular junctions).

The terms "patient," "individual," and "subject" are used interchangeably. As used herein, they mean any mammal. In some embodiments, the mammal is a human. In some embodiments, the mammal is a non-human, including farm animals (cattle, hogs, horses, goats, sheep, etc.), companion animals (dogs, cats, etc.), and research animals (mice and rats).

The term "pharmaceutically acceptable" as used herein, refers to a material that does not abrogate the biological activity or properties of the agents described herein, such as binding to a desired target, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

As used herein, the terms "robotic surgery", "robot-assisted surgery", or "computer-assisted surgery" refer to surgical techniques involving robotic systems that control the movement of medical instruments to conduct a surgical procedure with precise, flexible, and/or minimally invasive actions designed to limit the amount of surgical trauma, blood loss, pain, scarring, and post-surgical patient recovery time and/or complications, such as infection at the surgical area. Examples of robotic surgery include those conducted using the da Vinci Surgical System (Intuitive Surgical, Sunnyvale, CA, USA) approved by the U.S. Food and Drug Administration in 2000.

The terms "surgery" or "surgical method" as used herein, refers to any method used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerve, such as placement of retractors during spinal surgery, electrically conducting cardiac tissue or nerve ablation, epidural injection, intrathecal injections, neuron or nerve blocks, implantation of devices such as neuron or nerve stimulators and implantation of pumps. These methods may also include biopsy or other invasive techniques for the collection of cell or tissue samples, such as for diagnostic purposes.

As used herein, the term "targeting molecule" refers to any agent (e.g., peptide, protein, nucleic acid polymer, aptamer, or small molecule) that associates with (e.g., binds to) a target of interest. The target of interest may be a nerve cell or an organ or tissue associated with one or more nerve cells or nerve structures. In some embodiments, the targeting molecule is any agent that associates with (e.g., binds to) a target comprising one or more neurons, nerves, or tissues or structures associated therewith, i.e. nerve tissues, nervous system tissues, nerve bundles, etc. It is understood that nerve and nerve-related targets include those associated with the brain and spinal cord of the central nervous system (CNS) and the nerves of the peripheral nervous system (PNS).

Also provided herein are methods of imaging nervous tissue tumors (neoplasms), including Gliomas, such as gliomatosis cerebri, Oligoastrocytomas, Choroid plexus papillomas, Ependymomas, Astrocytomas (Pilocytic astrocytomas and Glioblastoma multiforme), Dysembryoplastic neuroepithelial tumors, Oligodendrogliomas, Medulloblastomas, and Primitive neuroectodermal tumors; Neuroepitheliomatous tumors, such as Ganglioneuromas, Neuroblastomas, Atypical teratoid rhabdoid tumors, Retinoblastomas, and Esthesioneuroblastomas; and Nerve Sheath Tumors, such as Neurofibromas (Neurofibrosarcomas and Neurofibromatosis), Schwannomas, Neurinomas, Acoustic neuromas, and Neuromas.

Provided is a method of imaging a target area in a subject, the method comprising contacting the target area in the subject with a compound selected from those herein and detecting the compound in the target area using fluorescence or near-infrared imaging.

Also provided is a method of imaging one or more nerves in a target area in a subject, the method comprising contacting the target area in the subject with a compound selected from those herein and detecting the compound in the target area using fluorescence imaging.

Also provided is a method of imaging one or more nerves in a target area in a subject, the method comprising contacting the target area in the subject with a compound selected from those herein and detecting the compound in the target area using near-infrared imaging.

Also provided is a method of minimizing nerve damage in a target area in a subject during a medical procedure, the method comprising the steps of:

a) contacting the target area in the subject with a compound selected from those herein;

b) detecting one or more nerves bound by the compound in the target area using fluorescence imaging; and c) minimizing actions of the medical procedure that may damage one or more nerves detected.

The method above may be used to identify nerves and minimize damage to them that may be caused by a medical procedure, including traumatic, thermal, and radiological damage or that are caused by the application of therapeutic agents, anesthetics, or anesthesia in the target area.

In some embodiments, the medical procedure referenced in the method above is a surgical procedure. In other embodiments, the medical procedure is a biopsy procedure, a radiological procedure, or the application of anesthetic or anesthesia to the subject. In further embodiments, the medical procedure in the method above is the insertion or implantation of a medical device, including a medical pump, stent, pacemaker, port, artificial joints, valves, screws, pins, plates, rods, cosmetic implants, neurostimulators, and the like.

Also provided is the use of any compound disclosed herein in the preparation of a composition for use in imaging one or more nerves in a subject using from near-infrared imaging.

Further provided is a kit comprising a container with a composition comprising a medically useful amount of a compound as described herein and a set of instructions for the use of the composition in a nerve imaging procedure.

General.

All reagents were purchased from Sigma Aldrich, Fisher Scientific, TCI, or Ark Pharm. Unless otherwise indicated, all commercially available starting materials were used directly without further purification. Analytical thin layer chromatography (TLC) was performed on Millipore ready-to-use plates with silica gel 60 (F254, 32-63 μm). Flash chromatography was performed on Sorbent Technologies silica gel for column chromatography or on a Biotage Isolera Flash System using SNAP Ultra cartridges. High-resolution mass spectra (HRMS) were measured on an Agilent 6244 time-of-flight LCMS with diode array detector VL+.

LCMS and Purity Characterization

Mass-to-charge ratio and purity of the benzo[c]phenoxazine compounds were characterized on an Agilent 6244 time-of-flight tandem liquid chromatography mass spectroscopy (LCMS) with diode array detector VL+. Sample (10 μL) was injected into a C18 column (Poroshell 120, 4.6×50 mm, 2.7 micron), and eluted with a solvent system of A ($H_2O$, 0.1% FA) and B (MeCN, 01.% FA) at 0.4 mL/min, from A/B=90/10 to 5/95 over 10 min, maintained at A/B=5/95 for additional 5 min. Ions were detected in positive ion mode by setting the capillary voltage at 4 kV and gas temperature at 350° C. Purity was calculated through area under the curve analysis of the absorbance at 254 nm.

UV-Vis Absorption and Fluorescence Spectroscopy.

UV-Vis and fluorescence spectra were collected on a SpectraMax M5 spectrometer with a Microplate reader (Molecular Devices, Sunnyvale, CA). All absorbance spectra were reference corrected. Extinction coefficient was calculated from Beer's Law plots of absorbance versus concentration. Relative quantum yields are reported using HITCI as reference. Excitation emission matrices (EEMs) were collected on a Cary Eclipse fluorescence spectrophotometer (Agilent Technologies), using 5-nm step size. The band pass for excitation and emission was 10 nm.

In FIG. 1, Excitation Emission Matrices (EEMs) of LGW05-25 in phosphate buffered saline solution containing 10% DMSO. Fluorophore concentration is 10 μM. The color scale of EEMs (C-J) are normalized to the maximum of the plot.

Physicochemical Property Calculation.

Marvin (17.21.0 ChemAxon) was used to calculate physicochemical properties (https://www.chemaxon.com).

Nerve-Specificity Screening using Direct/Topical Administration

Each compound was screened for its tissue-specificity using a previously published direct/topical administration strategy in murine brachial plexus and sciatic nerves.[1] Each compound from the benzo[c]phenoxazine library was formulated in the previously utilized co-solvent formulation (10% DMSO, 5% Kolliphor, 65% serum and 20% phosphate buffered saline) at 500 μM. 100 μL of the formulated Oxazine were incubated on the exposed brachial plexus or sciatic nerve for 5 minutes. The fluorophore containing solution was removed and the area was irrigated with saline 18 times to remove any unbound fluorophore. Co-registered fluorescence and color images were collected of each stained area 30 minutes after benzo[c]phenoxazine direct/topical administration using a custom built macroscopic imaging system with 710/75 nm excitation and 810 nm longpass emission filters. Custom written MatLab code was used to analyze the tissue specific fluorescence where regions of interest were selected on the nerve, muscle, cut muscle and adipose tissue using the white light images. These regions of interest were then analyzed on the co-registered matched fluorescence images permitting assessment of the nerve-to-muscle, nerve-to-cut muscle, and nerve-to-adipose ratios in blinded manner.

Nerve-Specificity Screening Using Systemic Administration

Each compound was screened for its tissue-specificity using a previously published systemic administration strategy in murine brachial plexus and sciatic nerves.[1] Each compound from the benzo[c]phenoxazine library was formulated in the previously utilized co-solvent formulation (10% DMSO, 5% Kolliphor, 65% serum and 20% phosphate buffered saline) at 2.5 mM. 200 μL of the formulated fluorophore was administered intravenously before exposing the brachial plexus and sciatic nerves. Co-registered fluorescence and color images were collected of each nerve site using a custom built macroscopic imaging system with 710/75 nm excitation and 810 nm longpass emission filters. Custom written MatLab code was used to analyze the tissue specific fluorescence where regions of interest were selected on the nerve, muscle and adipose tissue using the white light images. These regions of interest were then analyzed on the co-registered matched fluorescence images permitting assessment of the nerve to muscle and nerve to adipose ratios in blinded manner.

Resonance Structures

It will be understood that the fluorescent compounds described herein may exist in any possible resonance form. For instance, the compounds depicted as Formula I:

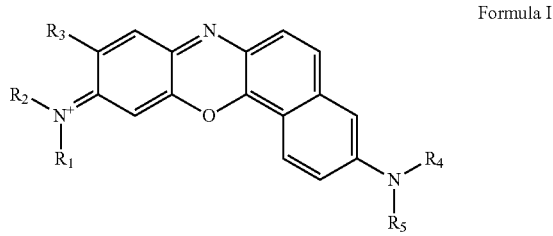

Formula I could be equally referred to using the structure:

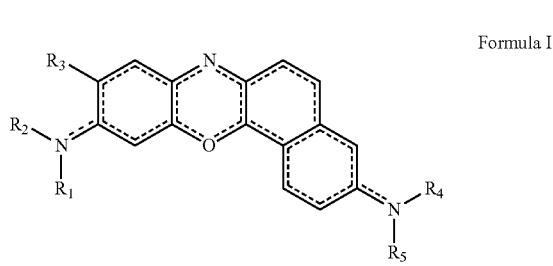

Formula I wherein, in each instance, the general listing of "- - - - -" indicates a single or a double bond as needed to satisfy valence requirements.

Chemical Synthesis

Scheme 1

Scheme 1: Synthetic route to LGW05-25. Reagents and conditions:
a) Ac$_2$O, H$_2$O, 50° C. to rt; b) BH$_3$—THF, THF, 0° C. to rt;
c) Ac$_2$O, H$_2$O, 50° C. to rt; d) BH$_3$—THF, THF, 0° C. to rt;
e) Ac$_2$O, H$_2$O, 50° C. to rt; f) BH$_3$—THF, THF, 0° C. to rt;
g) Compound 5, CuI, 2-picolinic acid, K$_3$PO$_4$, DMSO, 85° C.; h)
I) 2M HCl, p-nitrobenzenediazonium tetrafluoroborate, 0° C.;
II) K$_2$CO$_3$, 0° C.; i) TfOH, 100° C.

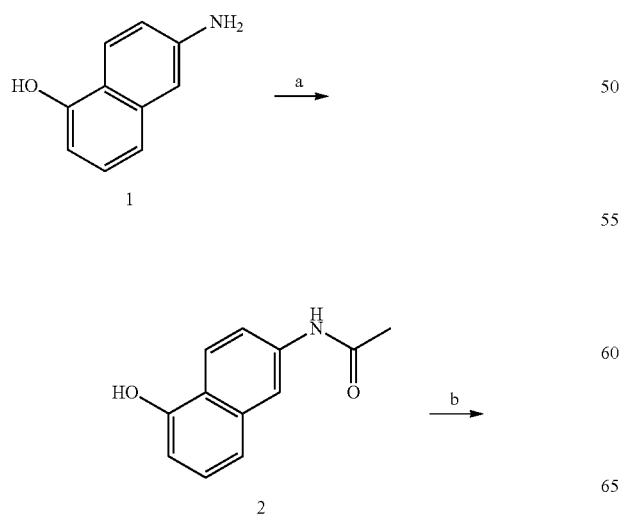

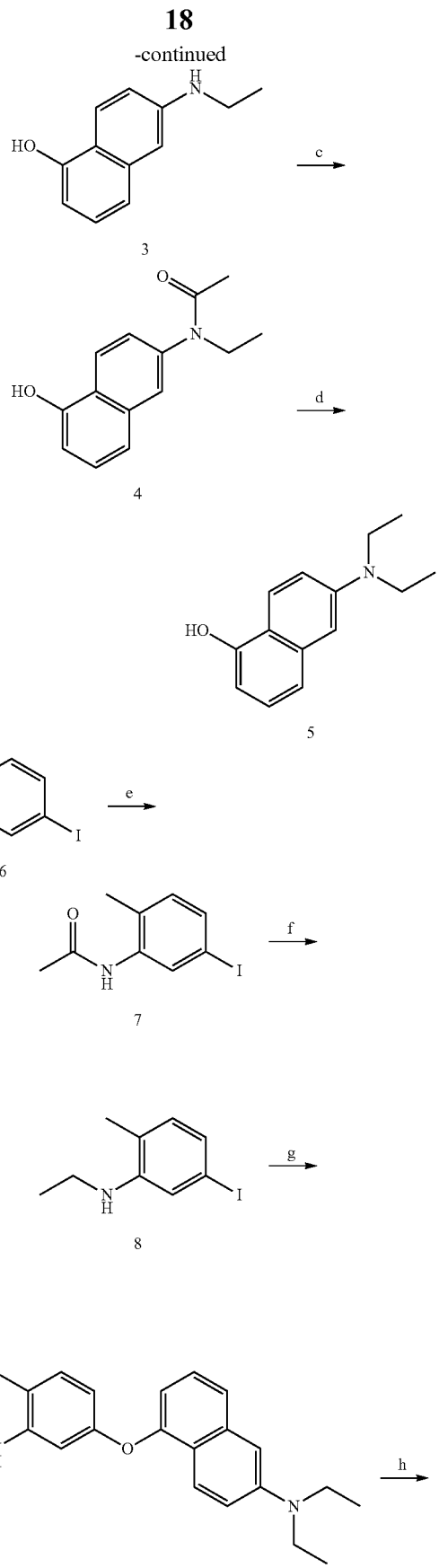

-continued

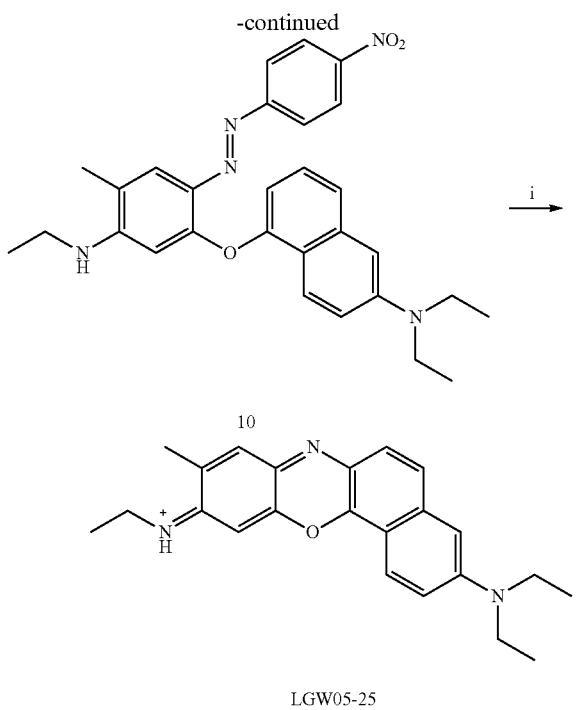

LGW05-25

N-(5-hydroxynaphthalen-2-yl)acetamide (2)

Compound 1 (4 g, 25.23 mmol) was suspended in 40 mL DI water, to which Acetic anhydride (9.50 mL, 100.51 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried to afford compound 2 (4.32 g, 85%) as a light gray solid, which was used for the next step without further purification.

6-(ethylamino)naphthalen-1-ol (3)

A solution of 2 (4 g, 19.88 mmol) in anhydrous THF (60 mL) was stirred in an ice bath under $N_2$ for 30 mins. Borane tetrahydrofuran complex solution (1 M, 60 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 3 (3.23 g, 87%) as a dark solid.

N-ethyl-N-(5-hydroxynaphthalen-2-yl)acetamide (4)

Compound 3 (3 g, 16.02 mmol) was suspended in 30 mL DI water, to which Acetic anhydride (6.06 mL, 64.09 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried to afford compound 4 (3.51 g, 96%) as a light gray solid, which was used for the next step without further purification.

6-(diethylamino)naphthalen-1-ol (5)

A solution of 4 (3.5 g, 15.27 mmol) in anhydrous THF (45 mL) was stirred in an ice bath under $N_2$ for 30 mins. Borane tetrahydrofuran complex solution (1 M, 45 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 5 (2.67 g, 81%) as a dark oil.

N-(5-iodo-2-methylphenyl)acetamide (7)

Compound 6 (2 g, 8.58 mmol) was dissolved in 2 mL DMSO, to which Acetic anhydride (2.43 mL, 25.75 mmol) was added dropwise. The reaction mixture was stirred in a water bath (50° C.) for 10 min, then stirred for additional 2 hours (h) at rt. 18 mL DI water was added to the reaction mixture, the resulting suspension was stirred overnight at rt. After which, the solid was collected via vacuum filtration and washed with small portions of DI water. The product was left in the funnel and air dried to afford compound 7 (2.09 g, 89%) as a light gray solid, which was used for the next step without further purification.

N-ethyl-5-iodo-2-methylaniline (8)

A solution of 7 (2.5 g, 9.09 mmol) in anhydrous THF (27 mL) was stirred in an ice bath under $N_2$ for 30 mins. Borane tetrahydrofuran complex solution (1 M, 27 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 8 (1.99 g, 84%) as a clear oil.

N,N-diethyl-5-(3-(ethylamino)-4-methylphenoxy)naphthalen-2-amine (9)

Compound 9 was synthesized using a slightly modified protocol published by Maiti and Buchwald.[2] An oven or flame dried, microwave glass tube was charged with a magnetic stir bar, compound 8 (260 mg, 0.996 mmol), 5 (195 mg, 0.905 mmol), CuI (17 mg, 0.091 mmol), 2-picolinic acid (22 mg, 0.181 mmol), and anhydrous $K_3PO_4$ (384 mg, 1.81 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 9 (258 mg, 82%) as a colorless oil.

(E)-N,N-diethyl-5-(5-(ethylamino)-4-methyl-2-((4-nitrophenyl)diazenyl)phenoxy)naphthalen-2-amine (10)

Compound 9 (0.175 g, 0.5 mmol) was dissolved in 1 mL MeOH. The solution was chilled in an ice bath, then was treated with HCl (2 M, 10 mL). After 15 mins, p-nitrobenzenediazonium tetrafluoroborate (0.13 g, 0.55 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 10 (0.223 g, 90%), which was used for the next step without further purification.

(Z)—N-(3-(diethylamino)-9-methyl-10H-benzo[c]phenoxazin-10-ylidene)ethanaminium (LGW05-25)

Compound 10 (0.1 g, 0.201 mmol) was added into a round bottom flask, and purged under $N_2$ stream. TfOH (1 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW05-25 (45 mg, 62%) as a dark green solid.

Scheme 2: Synthetic route to LGW06-65. Reagents and conditions:
a) CuI, 2-picolinic acid, $K_3PO_4$, DMSO, 85° C.; b)
I) 2M HCl, p-nitrobenzenediazonium tetrafluoroborate, 0° C.;
II) $K_2CO_3$, 0° C.; c) TfOH, 100° C.

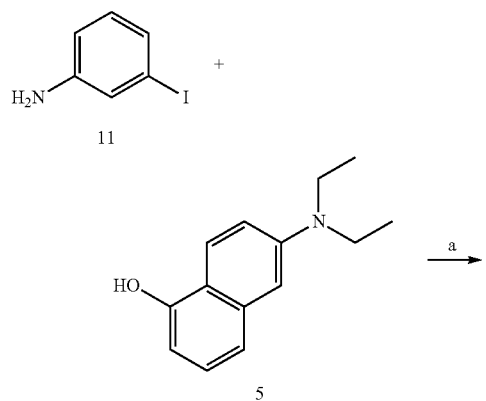

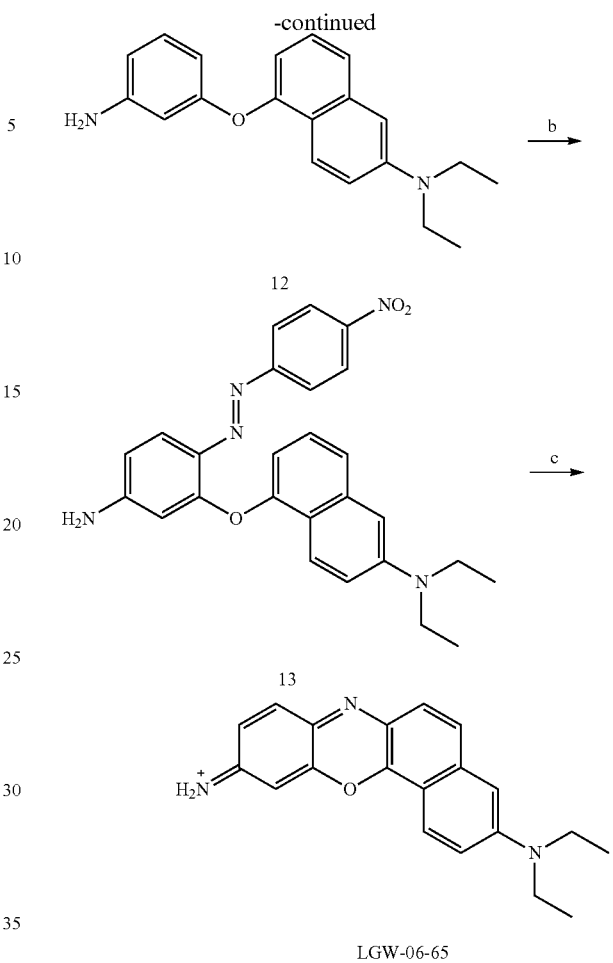

LGW-06-65

5-(3-aminophenoxy)-N,N-diethylnaphthalen-2-amine (12)

Compound 12 was synthesized using a slightly modified protocol published by Maiti and Buchwald.[2] An oven or flame dried, microwave glass tube was charged with a magnetic stir bar, compound 11 (190 mg, 0.868 mmol), 5 (170 mg, 0.789 mmol), CuI (15 mg, 0.079 mmol), 2-picolinic acid (19.5 mg, 0.158 mmol), and anhydrous $K_3PO_4$ (335 mg, 1.58 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 12 (178 mg, 74%) as a colorless oil.

(E)-5-(5-amino-2-((4-nitrophenyl)diazenyl)phenoxy)-N,N-diethylnaphthalen-2-amine (13)

Compound 12 (0.1 g, 0.326 mmol) was dissolved in 1 mL MeOH. The solution was chilled in an ice bath, then was treated with HCl (2 M, 10 mL). After 15 mins, p-nitrobenzenediazonium tetrafluoroborate (0.085 g, 0.359 mmol) was added to the solution above in 5 portions over 15 mins, then stirred at 0° C. for additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 13 (0.125 g, 81%), which was used for the next step without further purification.

3-(diethylamino)-10H-benzo[c]phenoxazin-10-iminium (LGW06-65)

Compound 13 (0.05 g, 0.11 mmol) was added into a round bottom flask, and purged under N$_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous Na$_2$SO$_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW06-65 (9 mg, 26%) as a dark green solid.

Scheme 3: Synthetic route to LGW06-83. Reagents and conditions: a) CuI, 2-picolinic acid, K$_3$PO$_4$, DMSO, 85° C; b) I) 2M p-nitrobenzenediazonium tetrafluoroborate, 0° C; II) K$_2$CO$_3$, 0° C; c) TfOH, 100° C.

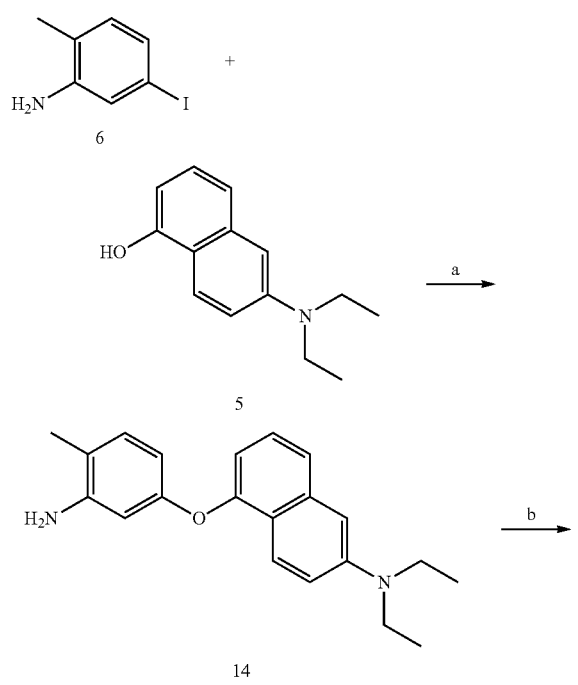

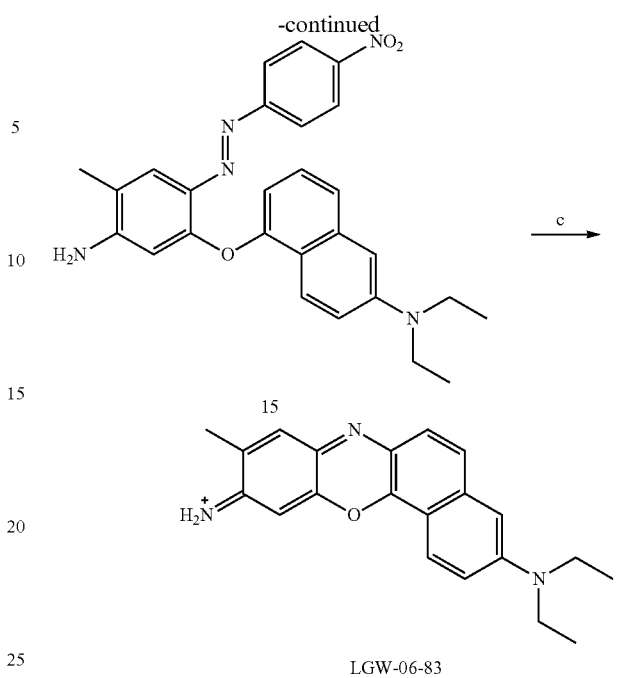

5-(3-amino-4-methylphenoxy)-N,N-diethylnaphthalen-2-amine (14)

Compound 14 was synthesized using a slightly modified protocol published by Maiti and Buchwald.[2] An oven or flame dried, microwave glass tube was charged with a magnetic stir bar, compound 6 (218 mg, 0.935 mmol), 5 (183 mg, 0.85 mmol), CuI (16 mg, 0.085 mmol), 2-picolinic acid (21 mg, 0.17 mmol), and anhydrous K$_3$PO$_4$ (361 mg, 1.7 mmol). The glass tube was evacuated under vacuum and backfilled with N$_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous Na$_2$SO$_4$, then concentrated in vacuo. The residue was purified by flash column chromatography with silica gel, using DCM/Hexane as eluent to give compound 14 (248 mg, 91%) as a colorless oil.

(E)-5-(5-amino-4-methyl-2-((4-nitrophenyl)diazenyl)phenoxy)-N,N-diethylnaphthalen-2-amine (15)

Compound 14 (0.14 g, 0.437 mmol) was dissolved in 1 mL MeOH. The solution was chilled in an ice bath, then was treated with HCl (2 M, 10 mL). After 15 mins, p-nitrobenzenediazonium tetrafluoroborate (0.109 g, 0.459 mmol) was added to the solution above in 5 portions over 15 mins, then stirred at 0° C. for additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 15 (0.184 g, 90%), which was used for the next step without further purification.

3-(diethylamino)-9-methyl-10H-benzo[c]phe-noxazin-10-iminium (LGW06-83)

Compound 15 (0.05 g, 0.106 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW06-83 (11 mg, 31%) as a dark green solid.

Scheme 4: Synthetic route to LGW06-84. Reagents and conditions:
a) $Ac_2O$, $H_2O$, 50° C. to rt; b) $BH_3$—THF, THF, 0° C. to rt;
c) Compound 5, CuI, 2-picolinic acid, $K_3PO_4$, DMSO, 85° C.; d)
I) 2M HCl, p-nitrobenzenediazonium tetrafluoroborate, 0° C.;
II) $K_2CO_3$, 0° C.; e) TfOH, 100° C.

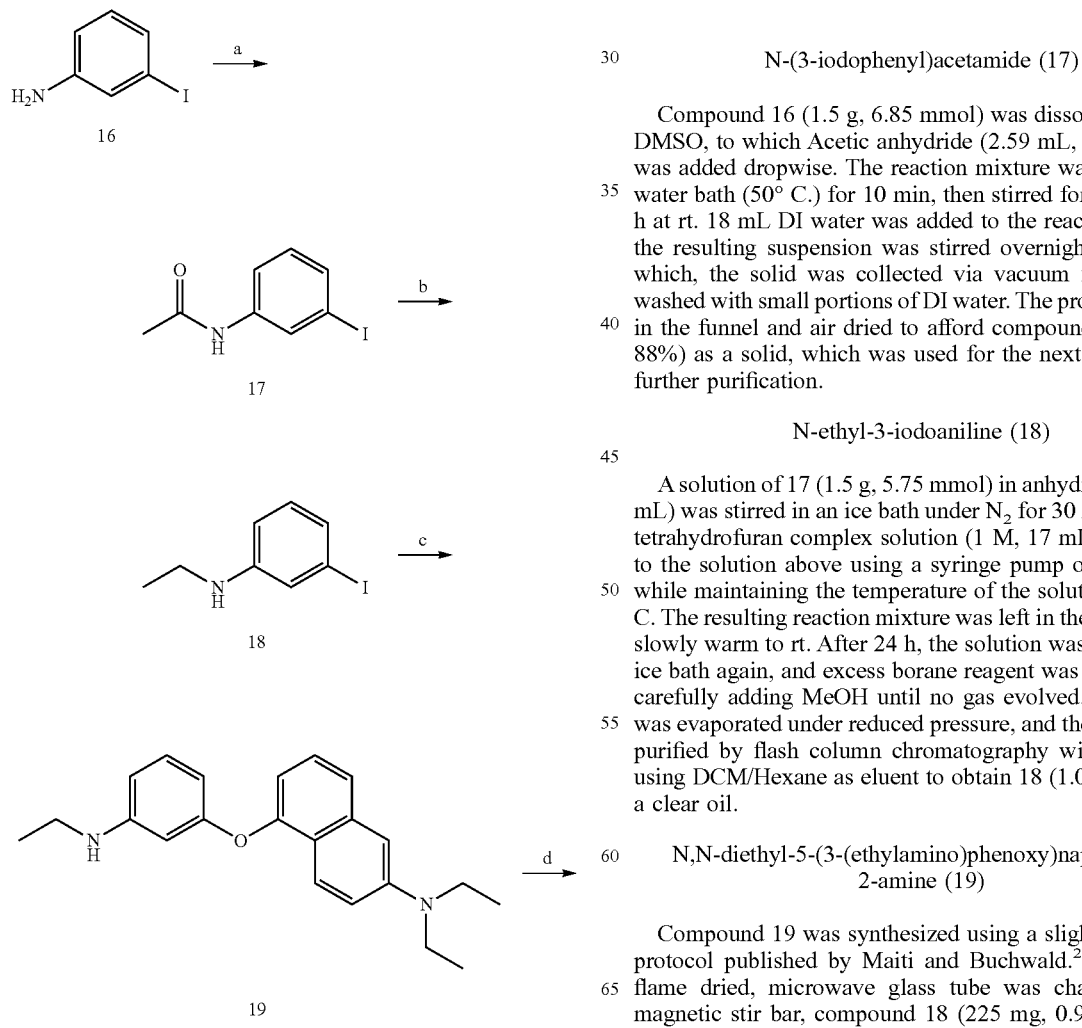

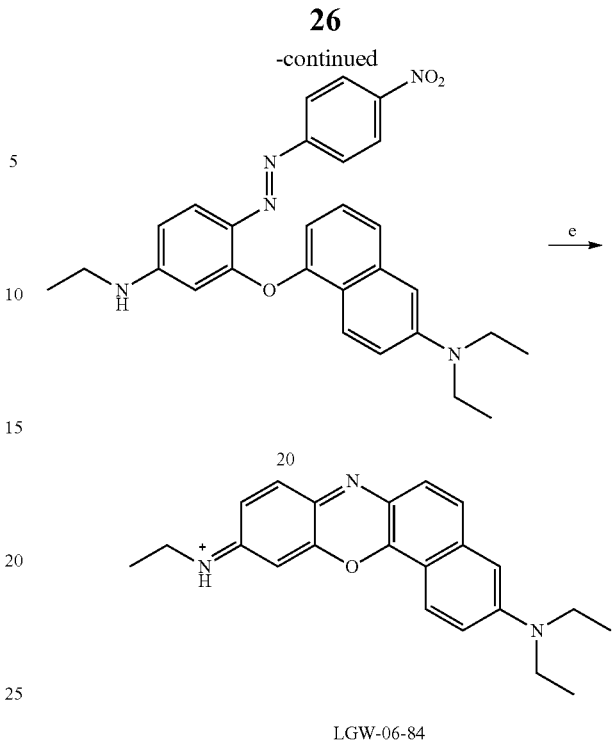

N-(3-iodophenyl)acetamide (17)

Compound 16 (1.5 g, 6.85 mmol) was dissolved in 2 mL DMSO, to which Acetic anhydride (2.59 mL, 27.39 mmol) was added dropwise. The reaction mixture was stirred in a water bath (50° C.) for 10 min, then stirred for additional 2 h at rt. 18 mL DI water was added to the reaction mixture, the resulting suspension was stirred overnight at rt. After which, the solid was collected via vacuum filtration and washed with small portions of DI water. The product was left in the funnel and air dried to afford compound 17 (1.57 g, 88%) as a solid, which was used for the next step without further purification.

N-ethyl-3-iodoaniline (18)

A solution of 17 (1.5 g, 5.75 mmol) in anhydrous THF (17 mL) was stirred in an ice bath under $N_2$ for 30 mins. Borane tetrahydrofuran complex solution (1 M, 17 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 18 (1.08 g, 76%) as a clear oil.

N,N-diethyl-5-(3-(ethylamino)phenoxy)naphthalen-2-amine (19)

Compound 19 was synthesized using a slightly modified protocol published by Maiti and Buchwald.[2] An oven or flame dried, microwave glass tube was charged with a magnetic stir bar, compound 18 (225 mg, 0.991 mmol), 5 (178 mg, 0.828 mmol), CuI (16 mg, 0.083 mmol), 2-picolinic acid (21 mg, 0.166 mmol), and anhydrous K₃PO₄ (351 mg, 1.66 mmol). The glass tube was evacuated under vacuum and backfilled with N₂ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous Na₂SO₄, then concentrated in vacuo. The residue was purified by flash column chromatography with silica gel, using DCM/Hexane as eluent to give compound 19 (173 mg, 62%) as a colorless oil.

(E)-N,N-diethyl-5-(5-(ethylamino)-2-((4-nitrophenyl)diazenyl)phenoxy)naphthalen-2-amine (20)

Compound 19 (0.150 g, 0.448 mmol) was dissolved in 1 mL MeOH. The solution was chilled in an ice bath, then was treated with HCl (2 M, 10 mL). After 15 mins, p-nitrobenzenediazonium tetrafluoroborate (0.112 g, 0.471 mmol) was added to the solution above in 5 portions over 15 mins, then stirred at 0° C. for additional 1 h. During which time, the color of the reaction mixture changed from orange to dark red. After which, the solution was carefully basified with solid K₂CO₃ until pH value of the solution rose above 8. The deep red precipitate was collected via vacuum filtration and washed with small portions of DI water. The product was left in the funnel and air dried overnight to afford compound 20 (0.189 g, 87%), which was used for the next step without further purification.

(E)-N-(3-(diethylamino)-10H-benzo[c]phenoxazin-10-ylidene)ethanaminium (LGW06-84)

Compound 20 (0.05 g, 0.103 mmol) was added into a round bottom flask, and purged under N₂ stream. TfOH (0.5 mL) was added to the reaction flask quickly, and the resulting solution was heated up to 100° C. After 2 h, the reaction mixture was cooled down to room temperature (rt) before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous Na₂SO₄, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW06-84 (15 mg, 42%) as a dark green solid.

Scheme 5: Synthetic route to LGW07-14. Reagents and conditions: a) CuI, LiI, DMEDA, dioxane, 110° C.; b) compound 5, CuI, 2-picolinic acid, K₃PO₄, DMSO, 85° C.; c) I) 2M HCl, p-nitrobenzenediazonium tetrafluoroborate, 0° C.; II) K₂CO₃, 0° C.; d) TfOH, 100° C.

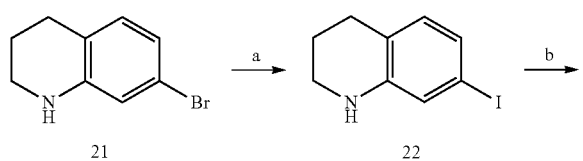

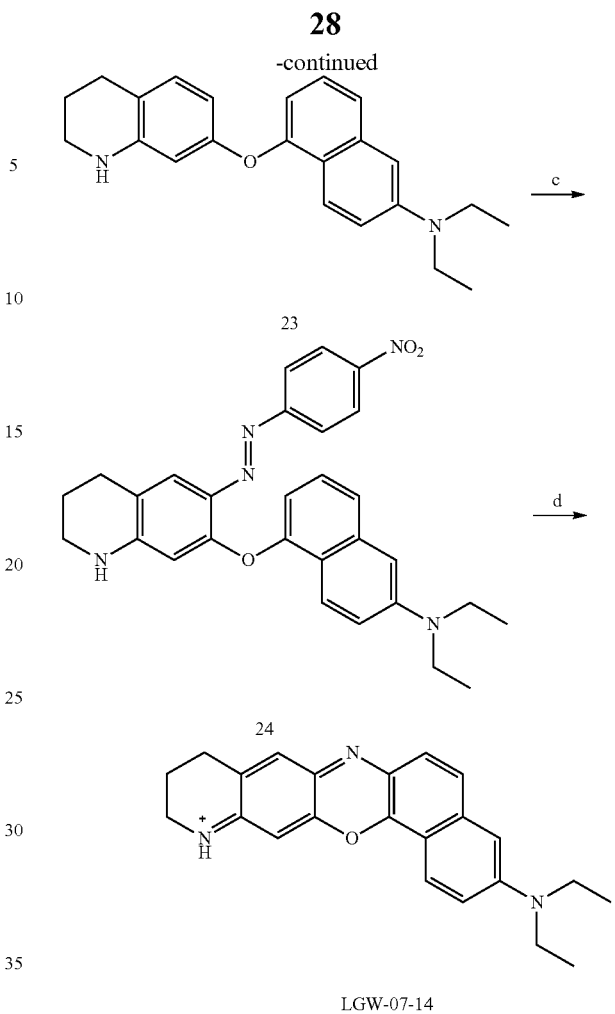

7-iodo-1,2,3,4-tetrahydroquinoline (22)

Compound 22 was synthesized using a slightly modified protocol published by Klapars and Buchwald.[3] An oven or flame dried, microwave glass tube was charged with a magnetic stir bar, compound 21 (600 mg, 2.83 mmol), CuI (54 mg, 0.283 mmol), and LiI (757 mg, 5.66 mmol). The glass tube was evacuated under vacuum and backfilled with N₂ 5 times, DMEDA (77 µL) was added into the reaction vessel quickly before the tube was sealed with a Teflon cap. Anhydrous 1,4-dioxane (3 mL) was delivered via a syringe. The reaction was then heated to 110° C. and stirred for 24 h. After cooling to rt, the reaction mixture was diluted with 10 mL sat. NH₄Cl solution and extracted with DCM (4×25 mL). The combined organic layers were washed with brine and dried over anhydrous Na₂SO₄, then concentrated in vacuo. The residue was purified by flash column chromatography with silica gel, using DCM/Hexane as eluent to give compound 22 (701 mg, 96%).

N,N-diethyl-5-((1,2,3,4-tetrahydroquinolin-7-yl)oxy)naphthalen-2-amine (23)

Compound 23 was synthesized using a slightly modified protocol published by Maiti and Buchwald.[2] An oven or flame dried, microwave glass tube was charged with a magnetic stir bar, compound 22 (290 mg, 1.12 mmol), 5 (219 mg, 1.02 mmol), CuI (19 mg, 0.102 mmol), 2-picolinic acid (25 mg, 0.204 mmol), and anhydrous $K_3PO_4$ (432 mg, 2.04 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 23 (292 mg, 83%) as a colorless oil.

(E)-N,N-diethyl-5-((6-(((4-nitrophenyl)diazenyl)-1,2,3,4-tetrahydroquinolin-7-yl)oxy)naphthalen-2-amine (24)

Compound 23 (0.160 g, 0.462 mmol) was dissolved in 1 mL MeOH. The solution was chilled in an ice bath, then was treated with HCl (2 M, 10 mL). After 15 mins, p-nitrobenzenediazonium tetrafluoroborate (0.115 g, 0.485 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 24 (0.196 g, 86%), which was used for the next step without further purification.

3-(diethylamino)-10,11-dihydro-9H-benzo[h]pyrido[3,2-b]phenoxazin-12-ium (LGW07-14)

Compound 24 (0.05 g, 0.101 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-14 (23 mg, 64%) as a dark green solid.

Scheme 6: Synthetic route to LGW07-16. a) Yb(OTf)$_3$, Acetone, rt; b) Compound 5, CuI, 2-picolinic acid, $K_3PO_4$, DMSO, 85° C.; c) I) 2M HCl, p-nitrobenzenediazonium tetrafluoroborate, 0° C.; II) $K_2CO_3$, 0° C.; d) TfOH, 100° C.

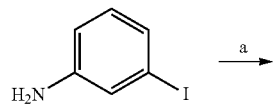

16

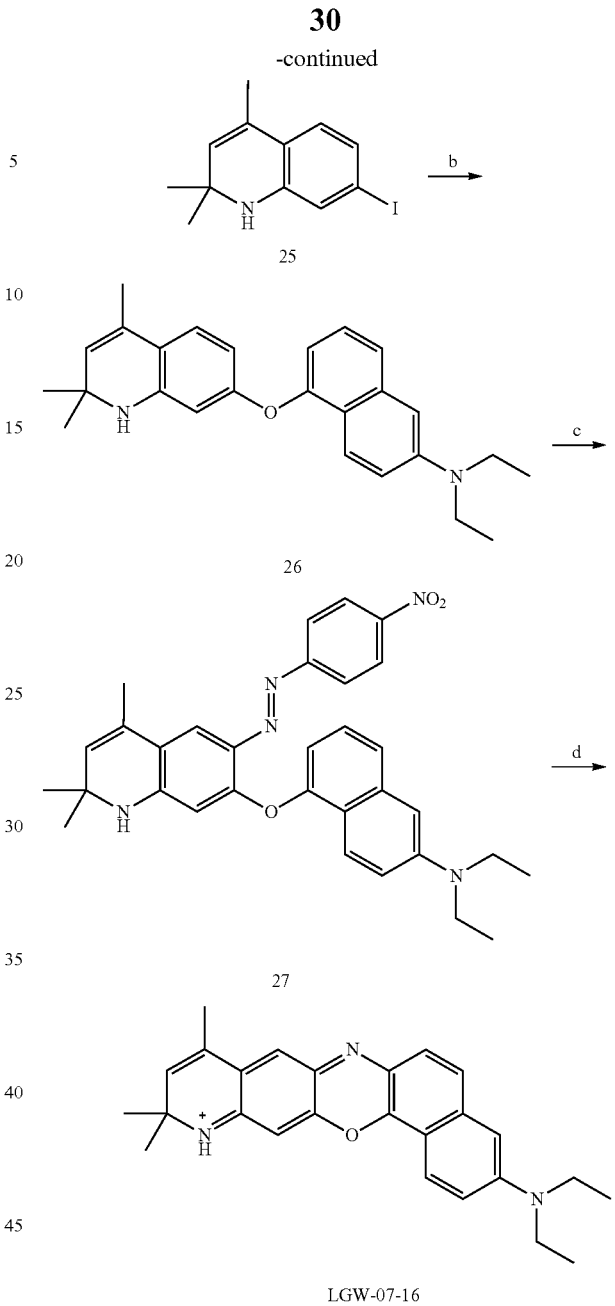

7-iodo-2,2,4-trimethyl-1,2-dihydroquinoline (25)

Compound 25 was synthesized using a modified protocol published by Belov Vladimir et al.[4] Compound 16 (0.550 mL, 4.57 mmol) was diluted in acetone (20 mL) under $N_2$, to the solution above ytterbium(III) triflate (0.283 g, 0.457 mmol) was added. The resulting solution was stirred at rt for 72 h. After which, the reaction mixture was concentrated under reduced pressure. The residue was dissolved in EtOAc, which was washed with water, brine, and dried over anhydrous $Na_2SO_4$. The organic solvent was removed using rotary evaporator. The crude product was purified by flash column chromatography, using DCM/Hexane as eluent to give compound 25 (0.65 g, 48%).

N,N-diethyl-5-((2,2,4-trimethyl-1,2-dihydroquinolin-7-yl)oxy)naphthalen-2-amine (26)

Compound 26 was synthesized using a slightly modified protocol published by Maiti and Buchwald.[2] An oven or flame dried, microwave glass tube was charged with a magnetic stir bar, compound 25 (330 mg, 1.10 mmol), 5 (216 mg, 1.0 mmol), CuI (19 mg, 0.10 mmol), 2-picolinic acid (25 mg, 0.20 mmol), and anhydrous $K_3PO_4$ (426 mg, 2.01 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 26 (277 mg, 71%) as a colorless oil.

(E)-N,N-diethyl-5-((2,2,4-trimethyl-6-((4-nitrophenyl)diazenyl)-1,2-dihydroquinolin-7-yl)oxy)naphthalen-2-amine (27)

Compound 26 (0.193 g, 0.499 mmol) was dissolved in 1 mL MeOH. The solution was chilled in an ice bath, then was treated with HCl (2 M, 10 mL). After 15 mins, p-nitrobenzenediazonium tetrafluoroborate (0.124 g, 0.524 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 27 (0.219 g, 82%), which was used for the next step without further purification.

3-(diethylamino)-9,11,11-trimethyl-11H-benzo[h]pyrido[3,2-b]phenoxazin-12-ium (LGW07-16)

Compound 27 (0.05 g, 0.093 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-16 (17 mg, 46%) as a dark green solid.

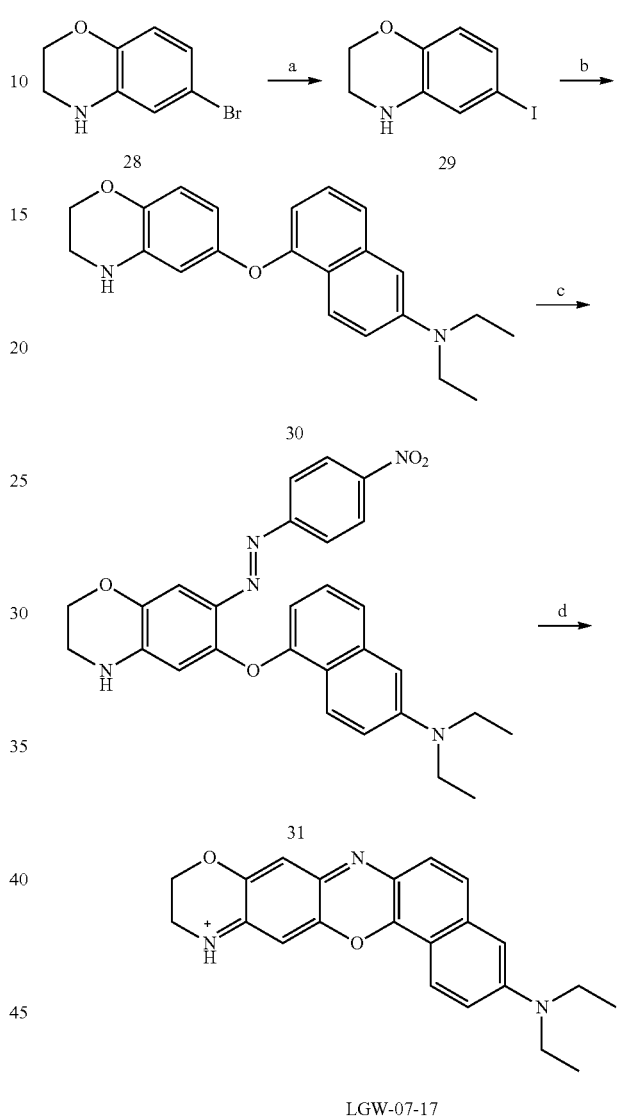

Scheme 7: Synthetic route to LGW07-17. Reagents and conditions: a) CuI, LiI, DMEDA, dioxane, 110° C.; b) Compound 5, CuI, 2-picolinic acid, $K_3PO_4$, DMSO, 85° C.; c) I) 2M HCl, p-nitrobenzenediazonium tetrafluoroborate, 0° C.; II) $K_2CO_3$, 0° C.; d) TfOH, 100° C.

6-iodo-3,4-dihydro-2H-benzo[b][1,4]oxazine (29)

Compound 29 was synthesized using a slightly modified protocol published by Klapars and Buchwald.[3] An oven or flame dried, microwave glass tube was charged with a magnetic stir bar, compound 28 (500 mg, 2.34 mmol), CuI (49 mg, 0.257 mmol), and LiI (688 mg, 5.14 mmol). The glass tube was evacuated under vacuum and backfilled with $N_2$ 5 times, DMEDA (55 µL) was added into the reaction vessel quickly before the tube was sealed with a Teflon cap. Anhydrous 1,4-dioxane (2.5 mL) was delivered via a syringe. The reaction was then heated to 110° C. and stirred for 24 h. After cooling to rt, the reaction mixture was diluted with 10 mL sat. $NH_4Cl$ solution and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 29 (554 mg, 91%).

5-((3,4-dihydro-2H-benzo[b][1,4]oxazin-6-yl)oxy)-N,N-diethylnaphthalen-2-amine (30)

Compound 30 was synthesized using a slightly modified protocol published by Maiti and Buchwald.[2] An oven or flame dried, microwave glass tube was charged with a magnetic stir bar, compound 29 (290 mg, 1.11 mmol), 5 (217 mg, 1.01 mmol), CuI (19 mg, 0.101 mmol), 2-picolinic acid (25 mg, 0.202 mmol), and anhydrous $K_3PO_4$ (429 mg, 2.02 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 30 (253 mg, 72%) as a colorless oil.

(E)-N,N-diethyl-5-((7-((4-nitrophenyl)diazenyl)-3,4-dihydro-2H-benzo[b][1,4]oxazin-6-yl)oxy)naphthalen-2-amine (31)

Compound 30 (0.130 g, 0.373 mmol) was dissolved in 1 mL MeOH. The solution was chilled in an ice bath, then was treated with HCl (2 M, 10 mL). After 15 mins, p-nitrobenzenediazonium tetrafluoroborate (0.093 g, 0.392 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 31 (0.175 g, 94%), which was used for the next step without further purification.

3-(diethylamino)-10,11-dihydrobenzo[h][1,4]oxazino[2,3-b]phenoxazin-12-ium (LGW07-17)

Compound 31 (0.05 g, 0.101 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-17 (19 mg, 53%) as a dark solid.

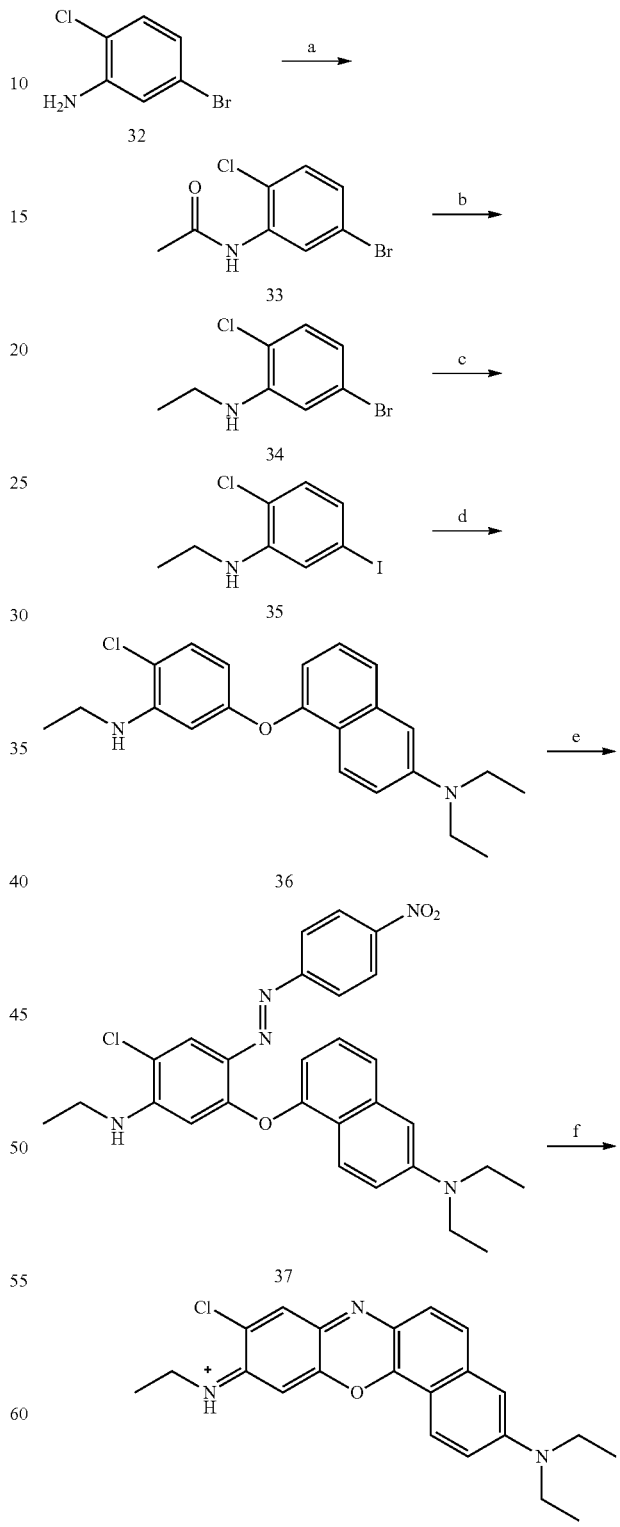

Scheme 8: Synthetic route to LGW07-48. Reagents and conditions: a) $Ac_2O$, $H_2O$, 50° C. to rt; b) $BH_3$-THF, THF, 0° C to rt; c) CuI, LiI, DMEDA, dioxane, 110° C; d) Compound 5, CuI, 2-picolinic acid, $K_3PO_4$, DMSO, 85° C; e) I) 2M HCl, p-nitrobenzenediazonium tetrafluoroborate, 0° C; II) $K_2CO_3$, 0° C; f) TfOH, 100° C.

N-(5-bromo-2-chlorophenyl)acetamide (33)

Compound 32 (2 g, 9.69 mmol) was dissolved in 2 mL DMSO, to which Acetic anhydride (3.66 mL, 38.75 mmol) was added dropwise. The reaction mixture was stirred in a water bath (50° C.) for 10 min, then stirred for additional 2 h at rt. 18 mL DI water was added to the reaction mixture, the resulting suspension was stirred overnight at rt. After which, the solid was collected via vacuum filtration and washed with small portions of DI water. The product was left in the funnel and air dried to afford compound 33 (2.13 g, 88%) as a solid, which was used for the next step without further purification.

5-bromo-2-chloro-N-ethylaniline (34)

A solution of 33 (2.0 g, 8.05 mmol) in anhydrous THF (24 mL) was stirred in an ice bath under $N_2$ for 30 mins. Borane tetrahydrofuran complex solution (1 M, 24 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 34 (1.77 g, 94%).

2-chloro-N-ethyl-5-iodoaniline (35)

Compound 35 was synthesized using a slightly modified protocol published by Klapars and Buchwald.[3] An oven or flame dried, microwave glass tube was charged with a magnetic stir bar, compound 34 (1.20 g, 5.12 mmol), CuI (98 mg, 0.512 mmol), and LiI (1.37 g, 10.23 mmol). The glass tube was evacuated under vacuum and backfilled with $N_2$ 5 times, DMEDA (121 µL) was added into the reaction vessel quickly before the tube was sealed with a Teflon cap. Anhydrous 1,4-dioxane (5 mL) was delivered via a syringe. The reaction was then heated to 110° C. and stirred for 24 h. After cooling to rt, the reaction mixture was diluted with 10 mL sat. $NH_4Cl$ solution and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 35 (1.25 g, 87%).

5-(4-chloro-3-(ethylamino)phenoxy)-N,N-diethyl-naphthalen-2-amine (36)

Compound 36 was synthesized using a slightly modified protocol published by Maiti and Buchwald.[2] An oven or flame dried, microwave glass tube was charged with a magnetic stir bar, compound 35 (315 mg, 1.12 mmol), 5 (219 mg, 1.02 mmol), CuI (19 mg, 0.102 mmol), 2-picolinic acid (25 mg, 0.203 mmol), and anhydrous $K_3PO_4$ (432 mg, 2.03 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 36 (316 mg, 84%) as a colorless oil.

(E)-5-(4-chloro-5-(ethylamino)-2-((4-nitrophenyl)diazenyl)phenoxy)-N,N-diethylnaphthalen-2-amine (37)

Compound 36 (0.150 g, 0.407 mmol) was dissolved in 1 mL MeOH. The solution was chilled in an ice bath, then was treated with HCl (2 M, 10 mL). After 15 mins, p-nitrobenzenediazonium tetrafluoroborate (0.101 g, 0.427 mmol) was added to the solution above in 5 portions over 15 mins, stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 37 (0.187 g, 89%), which was used for the next step without further purification.

(Z)—N-(9-chloro-3-(diethylamino)-10H-benzo[c]phenoxazin-10-ylidene)ethanaminium (LGW07-48)

Compound 37 (0.05 g, 0.097 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-48 (15 mg, 41%) as a dark green solid.

Scheme 9: Synthetic route to LGW07-50. Reagents and conditions: a) $Ac_2O$, $H_2O$, 50° C. to rt; b) $BH_3$—THF, THF, 0° C. to rt; c) CuI, LiI, DMEDA, dioxane, 110° C.; d) Compound 5, CuI, 2-picolinic acid, $K_3PO_4$, DMSO, 85° C.; e) I) 2M HCl, p-nitrobenzenediazonium tetrafluoroborate, 0° C.; II) $K_2CO_3$, 0° C.; f) TfOH, 100° C.

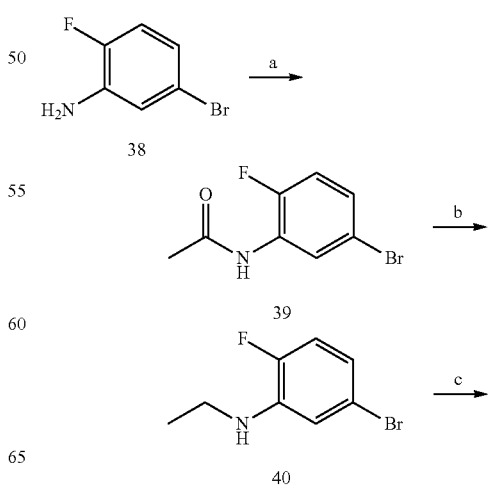

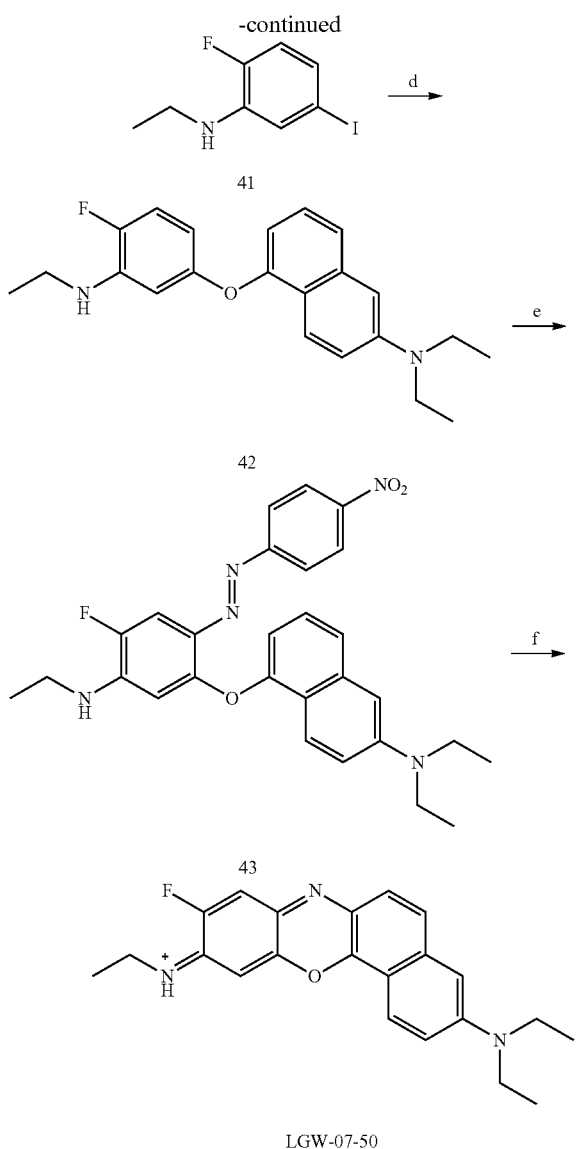

LGW-07-50

N-(5-bromo-2-fluorophenyl)acetamide (39)

Compound 38 (2 g, 10.53 mmol) was dissolved in 2 mL DMSO, to which Acetic anhydride (3.97 mL, 42.1 mmol) was added dropwise. The reaction mixture was stirred in a water bath (50° C.) for 10 min, then stirred for additional 2 hours at rt. 18 mL DI water was added to the reaction mixture, the resulting suspension was stirred overnight at rt. After which, the solid was collected via vacuum filtration and washed with small portions of DI water. The product was left in the funnel and air dried to afford compound 39 (1.99 g, 81%) as a solid, which was used for the next step without further purification.

5-bromo-N-ethyl-2-fluoroaniline (40)

A solution of 39 (1.5 g, 6.46 mmol) in anhydrous THF (19 mL) was stirred in an ice bath under $N_2$ for 30 mins. Borane tetrahydrofuran complex solution (1 M, 19 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 40 (1.28 g, 91%).

N-ethyl-2-fluoro-5-iodoaniline (41)

Compound 41 was synthesized using a slightly modified protocol published by Klapars and Buchwald.[3] An oven or flame dried, microwave glass tube was charged with a magnetic stir bar, compound 40 (1.0 g, 4.59 mmol), CuI (87 mg, 0.459 mmol), and LiI (1.23 g, 9.17 mmol). The glass tube was evacuated under vacuum and backfilled with $N_2$ 5 times, DMEDA (109 µL) was added into the reaction vessel quickly before the tube was sealed with a Teflon cap. Anhydrous 1,4-dioxane (4 mL) was delivered via a syringe. The reaction was then heated to 110° C. and stirred for 24 h. After cooling to rt, the reaction mixture was diluted with 10 mL sat. $NH_4Cl$ solution and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 41 (1.02 g, 84%).

N,N-diethyl-5-(3-(ethylamino)-4-fluorophenoxy) naphthalen-2-amine (42)

Compound 42 was synthesized using a slightly modified protocol published by Maiti and Buchwald.[2] An oven or flame dried, microwave glass tube was charged with a magnetic stir bar, compound 41 (180 mg, 0.679 mmol), 5 (133 mg, 0.617 mmol), CuI (12 mg, 0.062 mmol), 2-picolinic acid (15 mg, 0.124 mmol), and anhydrous $K_3PO_4$ (262 mg, 1.23 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 42 (174 mg, 80%) as a colorless oil.

(E)-N,N-diethyl-5-(5-(ethylamino)-4-fluoro-2-((4-nitrophenyl)diazenyl)phenoxy)naphthalen-2-amine (43)

Compound 42 (0.150 g, 0.426 mmol) was dissolved in 1 mL MeOH. The solution was chilled in an ice bath, then was treated with HCl (2 M, 10 mL). After 15 mins, p-nitrobenzenediazonium tetrafluoroborate (0.106 g, 0.447 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 43 (0.171 g, 80%), which was used for the next step without further purification.

(Z)—N-(3-(diethylamino)-9-fluoro-10H-benzo[c]phenoxazin-10-ylidene)ethanaminium (LGW07-50)

Compound 43 (0.05 g, 0.100 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-50 (12 mg, 33%) as a dark green solid.

Scheme 10: Synthetic route to LGW07-92. Reagents and conditions: a) MeI, $K_2CO_3$, MeCN, 80° C.; b) Compound 5, CuI, 2-picolinic acid, $K_3PO_4$, DMSO, 85° C.; c) I) 2M HCl, p-nitrobenzenediazonium tetrafluoroborate, 0° C.; II) $K_2CO_3$, 0° C.; d) TfOH, 100° C.

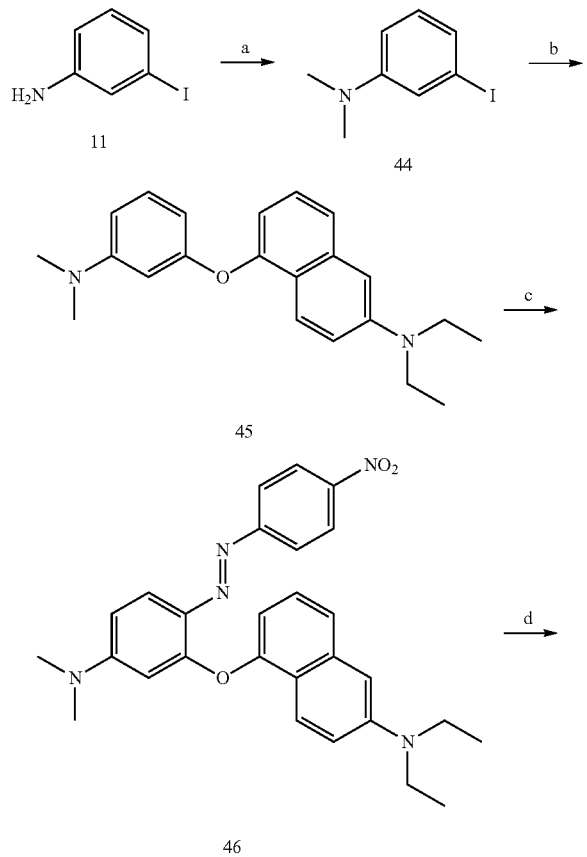

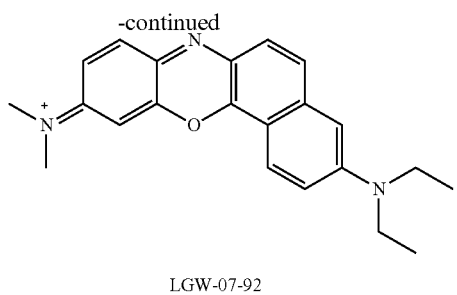

LGW-07-92

3-iodo-N,N-dimethylaniline (44)

To a suspension of compound 11 (1 g, 4.57 mmol) and $K_2CO_3$ (0.757 g, 5.48 mmol) in anhydrous MeCN (10 mL) under $N_2$, was added MeI (0.853 mL, 13.7 mmol) at rt. The reaction mixture was then heated up to 80° C. and stirred for additional 12 h. The solution was cooled down to rt and concentrated under reduced pressure. The crude product was diluted with DI water, and the resulting suspension was extracted with DCM (3×50 mL). The combined organic layers were rinsed with brine, dried over anhydrous $Na_2SO_4$. The solvent was removed using a rotary evaporator, and the residue was purified by flash column chromatography with silica gel, using EtOAc/Hexane as eluent to give compound 44 (0.87 g, 77%).

5-(3-(dimethylamino)phenoxy)-N,N-diethylnaphthalen-2-amine (45)

Compound 45 was synthesized using a slightly modified protocol published by Maiti and Buchwald.[2] An oven or flame dried, microwave glass tube was charged with a magnetic stir bar, compound 44 (200 mg, 0.810 mmol), 5 (158 mg, 0.736 mmol), CuI (14 mg, 0.074 mmol), 2-picolinic acid (18 mg, 0.147 mmol), and anhydrous $K_3PO_4$ (312 mg, 1.47 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 45 (202 mg, 82%) as a colorless oil.

(E)-5-(5-(dimethylamino)-2-((4-nitrophenyl)diazenyl)phenoxy)-N,N-diethylnaphthalen-2-amine (46)

Compound 45 (0.100 g, 0.299 mmol) was dissolved in 1 mL MeOH. The solution was chilled in an ice bath, then was treated with HCl (2 M, 10 mL). After 15 mins, p-nitrobenzenediazonium tetrafluoroborate (0.074 g, 0.314 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 46 (0.105 g, 72%), which was used for the next step without further purification.

N-(3-(diethylamino)-10H-benzo[c]phenoxazin-10-ylidene)-N-methylmethanaminium (LGW07-92)

Compound 46 (0.05 g, 0.103 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-92 (8 mg, 22%) as a dark green solid.

Scheme 11: Synthetic route to LGW07-98. Reagents and conditions: a) EtI, $K_2CO_3$, MeCN, 80° C.; b) Compound 5, CuI, 2-picolinic acid, $K_3PO_4$, DMSO, 85° C.; c) I) 2M HCl, p-nitrobenzenediazonium tetrafluoroborate, 0° C.; II) $K_2CO_3$, 0° C.; d) TfOH, 100° C.

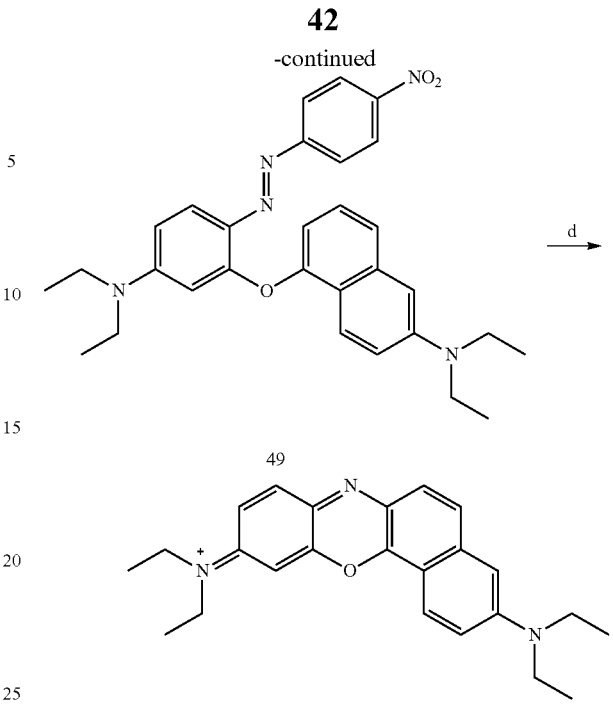

N,N-diethyl-3-iodoaniline (47)

To a suspension of compound 11 (1 g, 4.57 mmol) and $K_2CO_3$ (0.757 g, 5.48 mmol) in anhydrous MeCN (10 mL) under $N_2$, was added EtI (1.1 mL, 13.7 mmol) at rt. The reaction mixture was then heated up to 80° C. and stirred for additional 12 h. The solution was cooled down to rt and concentrated under reduced pressure. The crude product was diluted with DI water, and the resulting suspension was extracted with DCM (3×50 mL). The combined organic layers were rinsed with brine, dried over anhydrous $Na_2SO_4$. The solvent was removed using a rotary evaporator, and the residue was purified by flash column chromatography with silica gel, using EtOAc/Hexane as eluent to give compound 47 (0.94 g, 75%).

5-(3-(diethylamino)phenoxy)-N,N-diethylnaphthalen-2-amine (48)

Compound 48 was synthesized using a slightly modified protocol published by Maiti and Buchwald.[2] An oven or flame dried, microwave glass tube was charged with a magnetic stir bar, compound 47 (225 mg, 0.818 mmol), 5 (160 mg, 0.743 mmol), CuI (14 mg, 0.074 mmol), 2-picolinic acid (18 mg, 0.147 mmol), and anhydrous $K_3PO_4$ (316 mg, 1.49 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 48 (198 mg, 73%) as a colorless oil.

(E)-5-(5-(diethylamino)-2-((4-nitrophenyl)diazenyl) phenoxy)-N,N-diethylnaphthalen-2-amine (49)

Compound 48 (0.100 g, 0.276 mmol) was dissolved in 1 mL MeOH. The solution was chilled in an ice bath, then was treated with HCl (2 M, 10 mL). After 15 mins, p-nitrobenzenediazonium tetrafluoroborate (0.069 g, 0.290 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 49 (0.025 g, 18%), which was used for the next step without further purification.

N-(3-(diethylamino)-10H-benzo[c]phenoxazin-10-ylidene)-N-ethylethanaminium (LGW07-98)

Compound 46 (0.025 g, 0.049 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW07-98 (6 mg, 33%) as a dark green solid.

Scheme 12: Synthetic route to LGW08-06. Reagents and conditions: a) CuI, LiI, DMEDA, dioxane, 110° C.; b) Compound 5, CuI, 2-picolinic acid, $K_3PO_4$, DMSO, 85° C.; c) I) 2M HCl, p-nitrobenzenediazonium tetrafluoroborate, 0° C.; II) $K_2CO_3$, 0° C.; d) TfOH, 100° C.

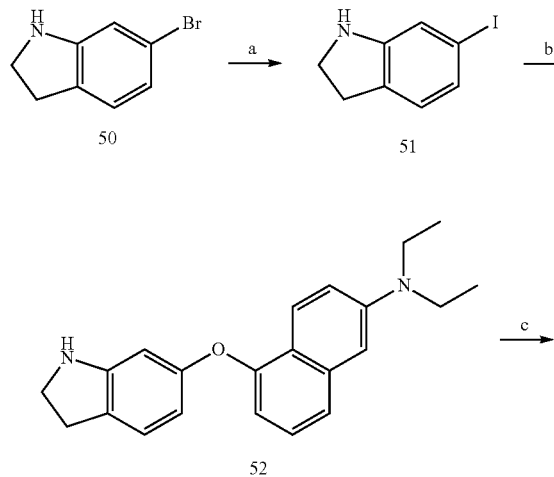

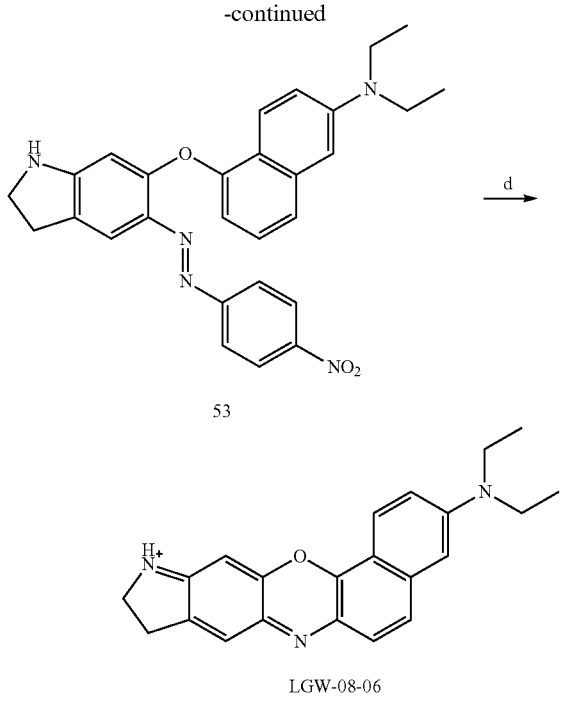

6-iodoindoline (51)

Compound 51 was synthesized using a slightly modified protocol published by Klapars and Buchwald.[3] An oven or flame dried, microwave glass tube was charged with a magnetic stir bar, compound 50 (1.0 g, 5.05 mmol), CuI (106 mg, 0.555 mmol), and LiI (1.49 g, 11.11 mmol). The glass tube was evacuated under vacuum and backfilled with $N_2$ 5 times, DMEDA (120 µL) was added into the reaction vessel quickly before the tube was sealed with a Teflon cap. Anhydrous 1,4-dioxane (5 mL) was delivered via a syringe. The reaction was then heated to 110° C. and stirred for 24 h. After cooling to rt, the reaction mixture was diluted with 10 mL sat. $NH_4Cl$ solution and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 51 (1.03 g, 83%).

N,N-diethyl-5-(indolin-6-yloxy)naphthalen-2-amine (52)

Compound 52 was synthesized using a slightly modified protocol published by Maiti and Buchwald.[2] An oven or flame dried, microwave glass tube was charged with a magnetic stir bar, compound 51 (240 mg, 0.98 mmol), 5 (201 mg, 0.934 mmol), CuI (18 mg, 0.093 mmol), 2-picolinic acid (23 mg, 0.187 mmol), and anhydrous $K_3PO_4$ (396 mg, 1.87 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 52 (265 mg, 85%) as a colorless oil.

(E)-N,N-diethyl-5-((5-((4-nitrophenyl)diazenyl)indolin-6-yl)oxy)naphthalen-2-amine (53)

Compound 52 (0.100 g, 0.301 mmol) was dissolved in 1 mL MeOH. The solution was chilled in an ice bath, then was treated with HCl (2 M, 10 mL). After 15 mins, p-nitrobenzenediazonium tetrafluoroborate (0.078 g, 0.331 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 53 (0.113 g, 78%), which was used for the next step without further purification.

3-(diethylamino)-9,10-dihydrobenzo[h]pyrrolo[3,2-b]phenoxazin-11-ium (LGW08-06)

Compound 53 (0.05 g, 0.104 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW08-06 (17 mg, 48%) as a dark solid.

Scheme 13: Synthetic route to LGW08-35. Reagents and conditions:
a) $Ac_2O$, $H_2O$, 50° C. to rt; b) $BH_3$—THF, THF, 0° C. to rt;
c) CuI, LiI, DMEDA, dioxane, 110° C.; d) Compound 5, CuI, 2-picolinic acid, $K_3PO_4$, DMSO, 85° C.; e) I) 2M HCl, p-nitrobenzenediazonium tetrafluoroborate, 0° C.;
II) $K_2CO_3$, 0° C.; f) TfOH, 100° C.

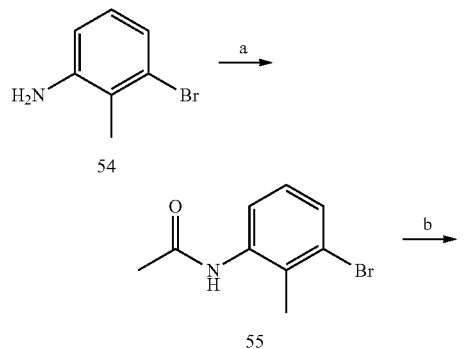

N-(3-bromo-2-methylphenyl)acetamide (55)

Compound 54 (4 g, 21.5 mmol) was dissolved in 4 mL DMSO, to which Acetic anhydride (8.11 mL, 86.0 mmol) was added dropwise. The reaction mixture was stirred in a water bath (50° C.) for 10 min, then stirred for additional 2 h at rt. 36 mL DI water was added to the reaction mixture, the resulting suspension was stirred overnight at rt. After which, the solid was collected via vacuum filtration and washed with small portions of DI water. The product was left in the funnel and air dried to afford Compound 55 (4.48 g, 91%) as a solid, which was used for the next step without further purification.

3-bromo-N-ethyl-2-methylaniline (56)

A solution of 55 (2.0 g, 8.77 mmol) in anhydrous THF (26 mL) was stirred in an ice bath under N$_2$ for 30 mins. Borane tetrahydrofuran complex solution (1 M, 26 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 56 (1.67 g, 89%).

N-ethyl-3-iodo-2-methylaniline (57)

Compound 57 was synthesized using a slightly modified protocol published by Klapars and Buchwald.[3] An oven or flame dried, microwave glass tube was charged with a magnetic stir bar, compound 56 (1.0 g, 4.67 mmol), CuI (98 mg, 0.514 mmol), and LiI (1.38 g, 10.28 mmol). The glass tube was evacuated under vacuum and backfilled with N$_2$ 5 times, DMEDA (111 µL) was added into the reaction vessel quickly before the tube was sealed with a Teflon cap. Anhydrous 1,4-dioxane (4 mL) was delivered via a syringe. The reaction was then heated to 110° C. and stirred for 24 h. After cooling to rt, the reaction mixture was diluted with 10 mL sat. NH$_4$Cl solution and extracted with DCM (4×25 mL). The combined organic layers were washed with brine and dried over anhydrous Na$_2$SO$_4$, then concentrated in vacuo. The residue was purified by flash column chromatography with silica gel, using DCM/Hexane as eluent to give compound 57 (1.05 g, 86%).

N,N-diethyl-5-(3-(ethylamino)-2-methylphenoxy)naphthalen-2-amine (58)

Compound 58 was synthesized using a slightly modified protocol published by Maiti and Buchwald.[2] An oven or flame dried, microwave glass tube was charged with a magnetic stir bar, compound 57 (174 mg, 0.664 mmol), 5 (130 mg, 0.604 mmol), CuI (12 mg, 0.06 mmol), 2-picolinic acid (15 mg, 0.121 mmol), and anhydrous K$_3$PO$_4$ (256 mg, 1.21 mmol). The glass tube was evacuated under vacuum and backfilled with N$_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous Na$_2$SO$_4$, then concentrated in vacuo. The residue was purified by flash column chromatography with silica gel, using DCM/Hexane as eluent to give compound 58 (189 mg, 90%) as a colorless oil.

(E)-N,N-diethyl-5-(3-(ethylamino)-2-methyl-6-((4-nitrophenyl)diazenyl)phenoxy)naphthalen-2-amine (59)

Compound 58 (0.200 g, 0.574 mmol) was dissolved in 1 mL MeOH. The solution was chilled in an ice bath, then was treated with HCl (2 M, 10 mL). After 15 mins, p-nitrobenzenediazonium tetrafluoroborate (0.143 g, 0.603 mmol) was added to the solution above in 5 portions over 15 mins, then stirred at 0° C. for additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 59 (0.266 g, 93%), which was used for the next step without further purification.

(E)-N-(3-(diethylamino)-11-methyl-10H-benzo[c]phenoxazin-10-ylidene)ethanaminium (LGW08-35)

Compound 59 (0.05 g, 0.101 mmol) was added into a round bottom flask, and purged under N$_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous Na$_2$SO$_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW08-35 (18 mg, 50%) as a dark green solid.

Scheme 14: Synthetic route to LGW08-46. Reagents and conditions: a) Ac$_2$O, H$_2$O, 50° C. to rt; b) BH$_3$-THF, THF, 0° C to rt; c) CuI, LiI, DMEDA, dioxane, 110° C; d) Compound 5, CuI, 2-picolinic acid, K$_3$PO$_4$, DMSO, 85° C; e) I) 2M HCl, p-nitrobenzenediazonium tetrafluoroborate, 0° C; II) K$_2$CO$_3$, 0° C; f) TfOH, 100° C.

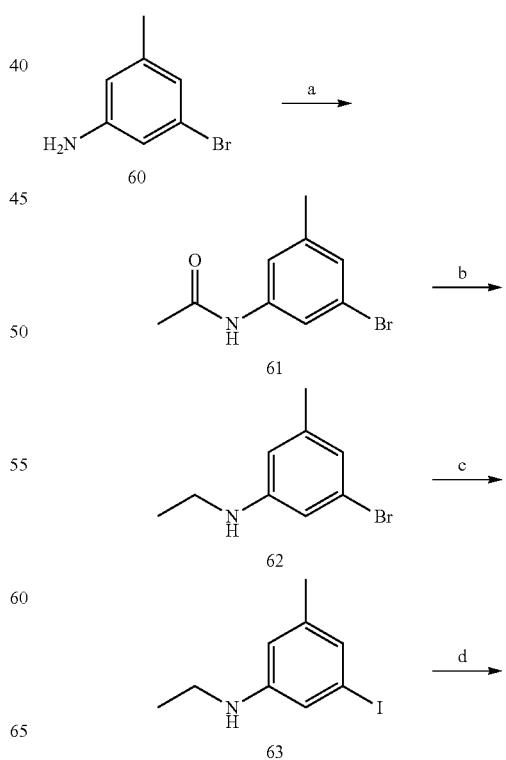

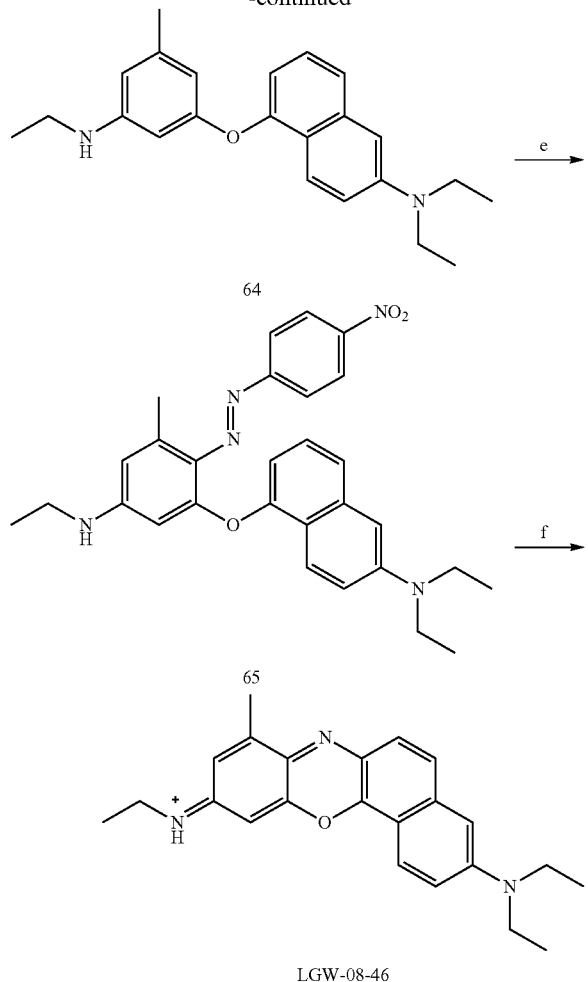

LGW-08-46

N-(3-bromo-5-methylphenyl)acetamide (61)

Compound 60 (4 g, 21.5 mmol) was dissolved in 4 mL DMSO, to which Acetic anhydride (8.11 mL, 86.0 mmol) was added dropwise. The reaction mixture was stirred in a water bath (50° C.) for 10 min, then stirred for additional 2 hours at rt. 36 mL DI water was added to the reaction mixture, the resulting suspension was stirred overnight at rt. After which, the solid was collected via vacuum filtration and washed with small portions of DI water. The product was left in the funnel and air dried to afford compound 61 (4.26 g, 87%) as a solid, which was used for the next step without further purification.

3-bromo-N-ethyl-5-methylaniline (62)

A solution of 61 (2.0 g, 8.77 mmol) in anhydrous THF (26 mL) was stirred in an ice bath under $N_2$ for 30 mins. Borane tetrahydrofuran complex solution (1 M, 26 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel, using DCM/Hexane as eluent to obtain 62 (1.72 g, 92%).

N-ethyl-3-iodo-5-methylaniline (63)

Compound 63 was synthesized using a slightly modified protocol published by Klapars and Buchwald.[3] An oven or flame dried, microwave glass tube was charged with a magnetic stir bar, compound 62 (1.0 g, 4.67 mmol), CuI (98 mg, 0.514 mmol), and LiI (1.38 g, 10.28 mmol). The glass tube was evacuated under vacuum and backfilled with $N_2$ 5 times, DMEDA (111 µL) was added into the reaction vessel quickly before the tube was sealed with a Teflon cap. Anhydrous 1,4-dioxane (4 mL) was delivered via a syringe. The reaction was then heated to 110° C. and stirred for 24 h. After cooling to rt, the reaction mixture was diluted with 10 mL sat. $NH_4Cl$ solution and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 63 (0.99 g, 81%).

N,N-diethyl-5-(3-(ethylamino)-5-methylphenoxy) naphthalen-2-amine (64)

Compound 64 was synthesized using a slightly modified protocol published by Maiti and Buchwald.[2] An oven or flame dried, microwave glass tube was charged with a magnetic stir bar, compound 63 (334 mg, 1.28 mmol), 5 (250 mg, 1.16 mmol), CuI (22 mg, 0.116 mmol), 2-picolinic acid (29 mg, 0.232 mmol), and anhydrous $K_3PO_4$ (493 mg, 2.32 mmol). The glass tube was evacuated under vacuum and backfilled with $N_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous $Na_2SO_4$, then concentrated in vacuo. The residue was purified by flash column chromatography with silica gel, using DCM/Hexane as eluent to give compound 64 (322 mg, 79%) as a colorless oil.

(E)-N,N-diethyl-5-(5-(ethylamino)-3-methyl-2-((4-nitrophenyl)diazenyl)phenoxy)naphthalen-2-amine (65)

Compound 64 (0.200 g, 0.574 mmol) was dissolved in 1 mL MeOH. The solution was chilled in an ice bath, then was treated with HCl (2 M, 10 mL). After 15 mins, p-nitrobenzenediazonium tetrafluoroborate (0.143 g, 0.603 mmol) was added to the solution above in 5 portions over 15 mins, then stirred at 0° C. for additional 1 h. During which time, the color of the reaction mixture changed from orange to dark red. After which, the solution was carefully basified with solid $K_2CO_3$ until pH value of the solution rose above 8. The deep red precipitate was collected via vacuum filtration and washed with small portions of DI water. The product was left in the funnel and air dried overnight to afford compound 65 (0.253 g, 89%), which was used for the next step without further purification.

(E)-N-(3-(diethylamino)-8-methyl-10H-benzo[c] phenoxazin-10-ylidene)ethanaminium (LGW08-46)

Compound 65 (0.05 g, 0.101 mmol) was added into a round bottom flask, and purged under $N_2$ stream. TfOH (0.5 mL) was added to the reaction flask quickly, and the resulting solution was heated up to 100° C. After 2 h, the reaction mixture was cooled down to rt before poured into a 25 mL ice cold water. To the solution above, NaOH solution (2 M) was added dropwise until the pH of the solution rose up to 4-5. The aqueous solution was extracted with DCM (4×25 mL). The combined organic layers were washed with brine and dried over anhydrous $Na_2SO_4$, then concentrated in vacuo. The residue was purified on a Biotage Isolera Flash System using SNAP Ultra cartridge with a mobile phase of DCM and MeOH containing 0.5% formic acid (gradient, 2-15% of MeOH in DCM). The fractions containing product were pooled and evaporated, affording LGW08-46 (23 mg, 64%) as a dark green solid.

REFERENCES

1. Barth, C. W.; Gibbs, S. L., Direct Administration of Nerve-Specific Contrast to Improve Nerve Sparing Radical Prostatectomy. *Theranostics* 2017, 7 (3), 573-593.
2. Maiti, D.; Buchwald, S. L., Orthogonal Cu- and Pd-based catalyst systems for the O- and N-arylation of aminophenols. *J Am Chem Soc* 2009, 131 (47), 17423-9.
3. Klapars, A.; Buchwald, S. L., Copper-Catalyzed Halogen Exchange in Aryl Halides: An Aromatic Finkelstein Reaction. *Journal of the American Chemical Society* 2002, 124 (50), 14844-14845.
4. Belov Vladimir, N.; Bossi Mariano, L.; Fölling, J.; Boyarskiy Vadim, P.; Hell Stefan, W., Rhodamine Spiroamides for Multicolor Single-Molecule Switching Fluorescent Nanoscopy. *Chemistry—A European Journal* 2009, 15 (41), 10762-10776.

In vivo nerve-specificity screening of the benzo[c]phenoxazine derivative library. Each compound was screened for its tissue-specificity using a direct administration strategy (Barth & Gibbs, *Theranostics* 7, 573-593 (2017)) where nerve contrast was examined in murine brachial plexus and sciatic nerves. The benzo[c]phenoxazine derivatives were solubilized for in vivo use in the previously described co-solvent formulation (Gibbs-Strauss et al., *Molecular imaging* 10, 91-101 (2011)). The previously optimized staining procedure was utilized (Gibbs et al., *PloS one* 8, e73493 (2013)), which is described briefly as follows. The brachial plexus and sciatic nerves were surgically exposed by removal of overlaying adipose and muscle tissues. The benzo[c]phenoxazine compound was formulated at 500 μM in the co-solvent formulation and 100 μL was incubated on the exposed brachial plexus or sciatic nerve for 5 minutes. The fluorophore containing solution was removed and the area was irrigated with saline nine times, followed by a five-minute incubation with blank formulation and then irrigation with saline nine more times to remove any unbound fluorophore. Images were acquired 30 minutes following completion of staining. Unstained nerve sites were used for all control images to quantify autofluorescence. Each benzo[c]phenoxazine derivative was screened in n=3 mice or 6 nerve sites/fluorophore. The quantified tissue fluorescence intensities following direct administration of the fluorophores were used to calculate nerve-to-muscle, nerve-to-cut muscle, and nerve-to-adipose ratios as metrics of nerve contrast. Five lead candidates were selected for further nerve-specificity screening studies via systemic administration, and they are LGW 05-25, LGW07-14, LGW07-92, LGW08-35, and LGW08-46. The dose and pharmacokinetics studies for the benzo[c]phenoxazine fluorophore library is described briefly as follows. Each of the lead candidates selected above were formulated in co-solvent formulation, where 500 nmol of each compound in 200 μL of solution were administered intravenously (IV), mice were sacrificed at 0.5, 1, 2, and 4 hour time points prior to imaging. Uninjected animals were used for all control images to quantify autofluorescence. Similarly to quantification protocol for the direct administration, the quantified tissue fluorescence intensities following systemic administration of the fluorophores were used to calculate nerve-to-muscle and nerve-to-adipose ratios as metrics of nerve contrast. Each candidate was screened in n=3 mice or 6 nerve sites/fluorophore with the two brachial plexus and two sciatic nerve sites being averaged together for a total of two replicates per animal, one of each nerve type.

Intraoperative fluorescence imaging systems. A custom-built small animal imaging system capable of real-time color and fluorescence imaging was used to acquire in vivo rodent images (Hackman et al., *Molecular pharmaceutics* (2015)). Briefly, the imaging system consisted of a QImaging EXi Blue monochrome camera (Surrey, British Columbia, CA) for fluorescence detection with a removable Bayer filter for collection of co-registered color and fluorescence images. A PhotoFluor II light source was focused onto the surgical field through a liquid light guide and used unfiltered for white light illumination. For fluorescence excitation, the PhotoFluor II was filtered with a 710±37.5 nm bandpass excitation filter. The resulting fluorescence was collected with a 810 nm longpass emission filter. All filters were obtained from Chroma Technology (Bellows Falls, VT). Camera and light source positions did not vary throughout the course of all imaging studies, allowing quantitative comparison of in vivo fluorescence intensities. Camera exposure times ranged from 5-5000 ms for fluorescence image collection.

Figure 3A:
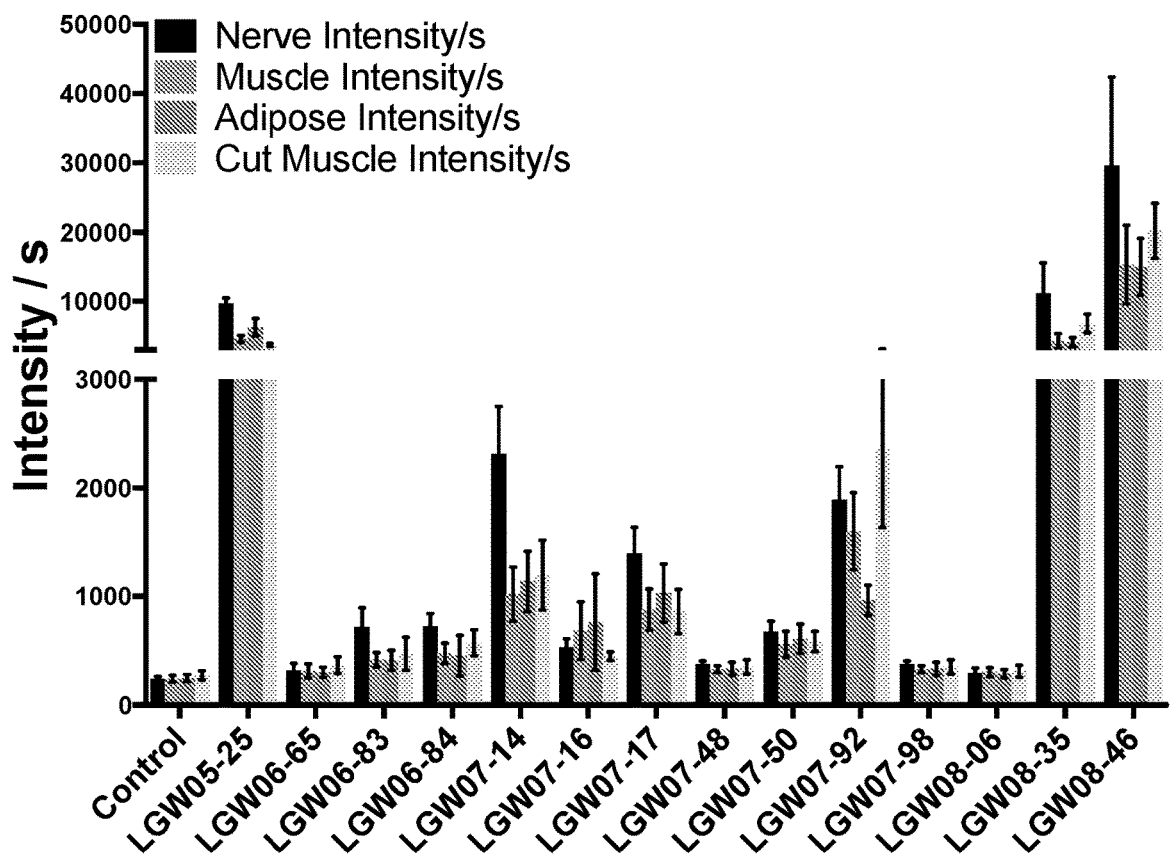
FIG. 3A provides a graph of averaged quantified fluorescence intensity per second following direct administration for nerve, adipose, and cut muscle tissues.
Figure 3B:
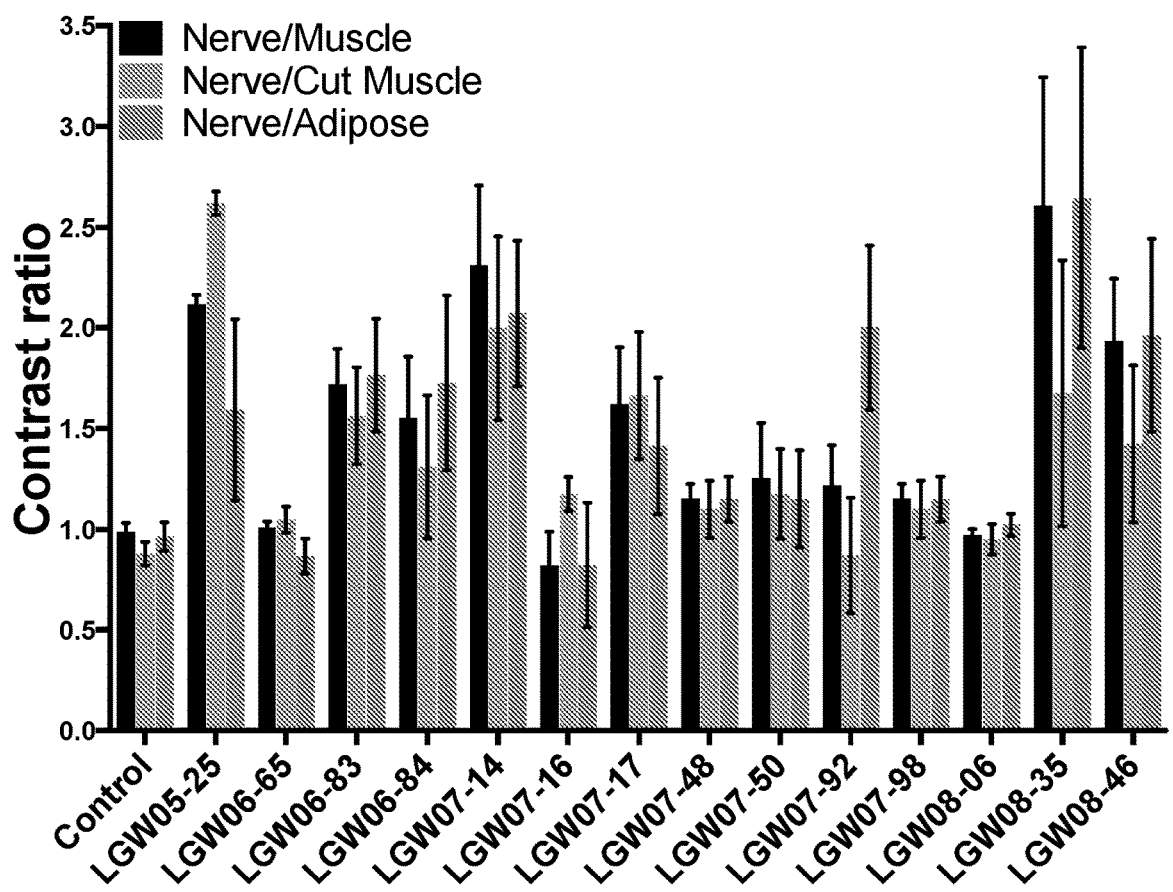
FIG. 3B provides a graph of calculated nerve-to-muscle, nerve-to-cut muscle, and nerve-to-adipose ratios determined following direct compound administration FIGS. 4A, 4B, and 4C provide graphs of averaged quantified fluorescence intensity per second for nerve (4A), muscle (4B), and adipose tissues (4C) following systemic administration.
Figure 4A:
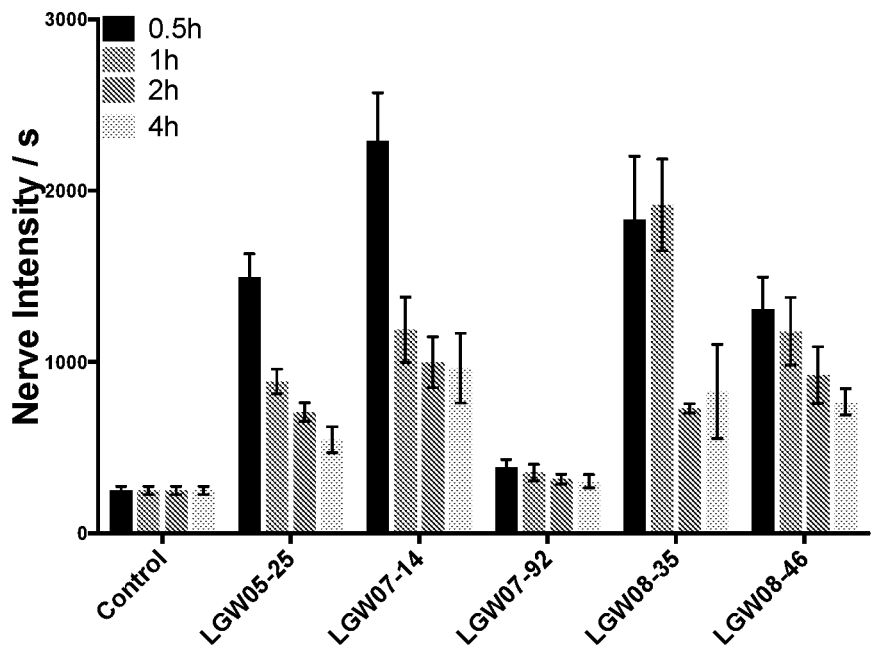
FIGS. 4D and 4E provide graphs representing the calculated nerve-to-muscle (4D) and nerve-to-adipose (4E) ratios following systemic administration.
Figure 4B:
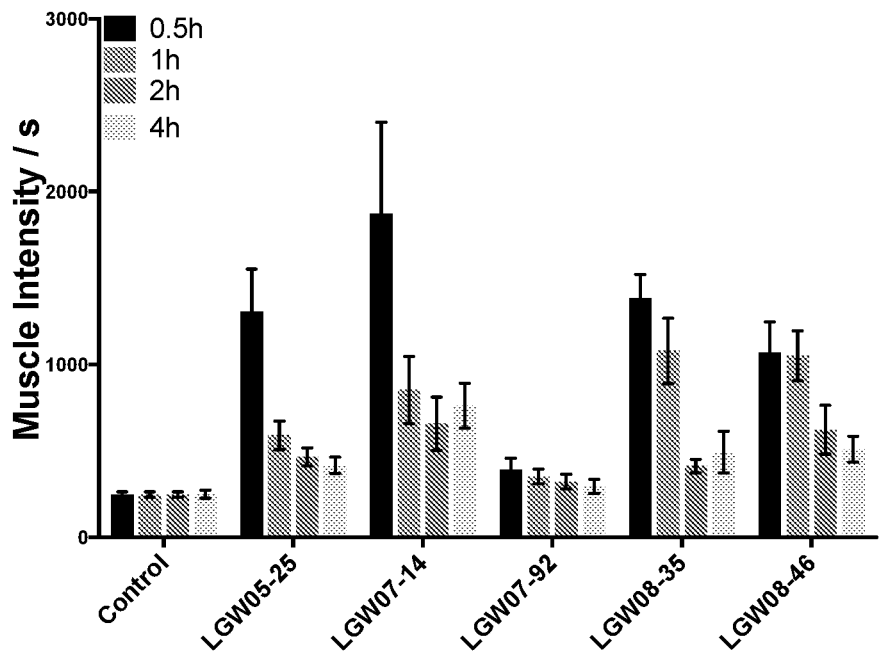
Figure 4C:
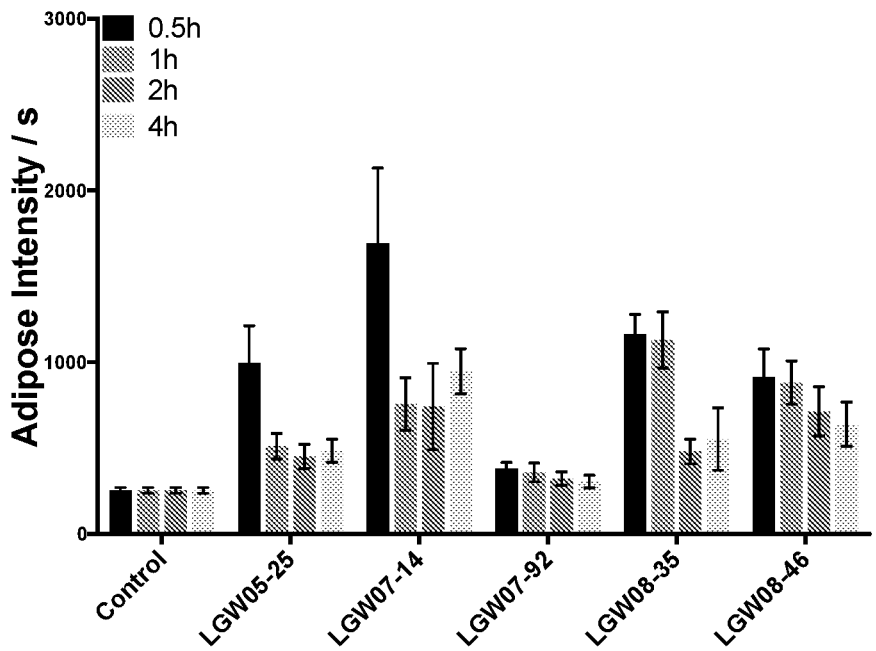
Figure 4D:
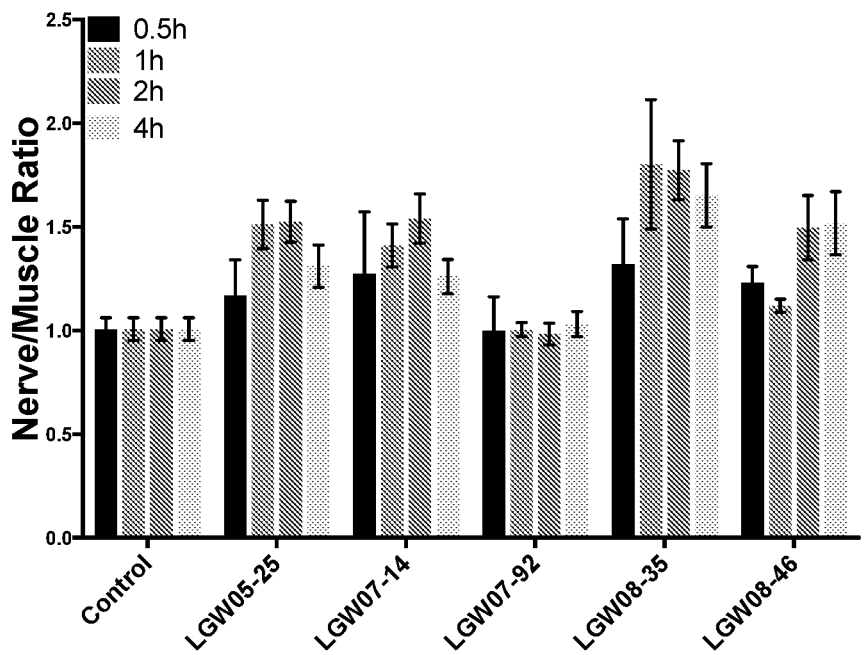
Figure 4E:
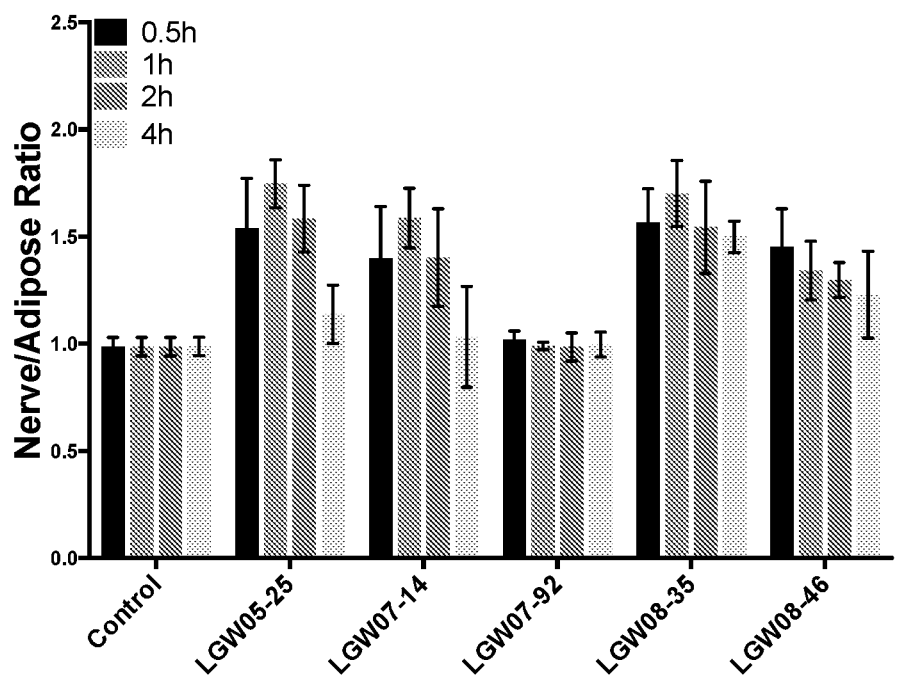

In vivo nerve-specificity screening of the benzo[c]phenoxazine derivative library via direct administration. As indicated in FIGS. 3A and 3B, the averaged quantified fluorescence intensity per second for the nerve, muscle, adipose, and cut muscle (3A). The calculated nerve-to-muscle, nerve-to-cut muscle, and nerve-to-adipose ratios (3B). Five lead candidates were selected for further nerve-specificity screening studies via systemic administration, and they are LGW 05-25, LGW07-14, LGW07-92, LGW08-35, and LGW08-46 (pointed by blue arrows).

In vivo nerve-specificity screening of the selected benzo[c]phenoxazine candidates via systemic administration. Mice were injected with 500 nmol of each screening candidate in co-solvent formulation and sacrificed at 0.5 h, 1 h, 2 h, and 4 h time pointes. The averaged quantified fluorescence intensity per second for the nerve, muscle, and adipose tissues (4A, 4B, and 4C). The calculated nerve-to-muscle, and nerve-to-adipose ratios (4D and 4E). Four compounds were selected as lead benzo[c]phenoxazine nerve-specific fluorophores following systemic administration, and they are LGW 05-25, LGW07-14, LGW08-35, and LGW08-46.

Note: Mice were injected with 500 nmol of each screening candidate in co-solvent formulation and sacrificed at 0.5 h, 1 h, 2 h, and 4 h time pointes. Lead candidates are selected following systemic administration, and they are LGW 05-25, LGW07-14, LGW08-35, and LGW08-46.

What is claimed:

1. A compound of Formula I:

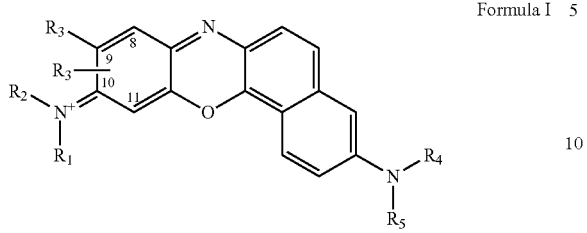

Formula I wherein $R_1$ is selected from hydrogen and $C_1$-$C_3$ alkyl;
$R_2$ is selected from hydrogen and $C_1$-$C_3$ alkyl;
$R_3$ is selected from the group of hydrogen, halogen, and $C_1$-$C_3$ alkyl;
or, when $R_3$ is bound to the 9-position carbon of the 10H-benzo[c]phenoxazine core, $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents; and
$R_4$ and $R_5$ are each independently selected from hydrogen and $C_1$-$C_3$ alkyl.

2. The compound of claim 1, wherein $R_1$ is hydrogen; $R_2$ is $C_1$-$C_3$ alkyl; $R_3$ is selected from the group of hydrogen, halogen, and $C_1$-$C_3$ alkyl; and $R_4$ and $R_5$ are each independently selected from hydrogen and $C_1$-$C_3$ alkyl.

3. The compound of claim 1, wherein $R_1$ is hydrogen; $R_2$ is $C_1$-$C_3$ alkyl; $R_3$ is selected from the group of hydrogen, F, Cl, and $C_1$-$C_3$ alkyl; and $R_4$ and $R_5$ are each independently selected from hydrogen and $C_1$-$C_3$ alkyl.

4. The compound of claim 1, wherein $R_1$ is hydrogen; $R_2$ is $C_1$-$C_3$ alkyl; $R_3$ is selected from the group of hydrogen, F, Cl, and $C_1$-$C_3$ alkyl; and $R_4$ and $R_5$ are each independently $C_1$-$C_3$ alkyl.

5. The compound of claim 1, wherein $R_1$ is hydrogen; $R_2$ is $C_1$-$C_2$ alkyl; $R_3$ is selected from the group of hydrogen, F, Cl, and $C_1$-$C_2$ alkyl; and $R_4$ and $R_5$ are each independently $C_1$-$C_2$ alkyl.

6. The compound of claim 1, wherein $R_1$ is selected from hydrogen and $C_1$-$C_3$ alkyl;
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents; and
$R_4$ and $R_5$ are each independently selected from hydrogen and $C_1$-$C_3$ alkyl.

7. The compound of claim 1, wherein $R_1$ is selected from hydrogen and $C_1$-$C_3$ alkyl;
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_2$ alkyl substituents; and
$R_4$ and $R_5$ are each independently selected from hydrogen and $C_1$-$C_2$ alkyl.

8. The compound of claim 1 comprising Formula II:

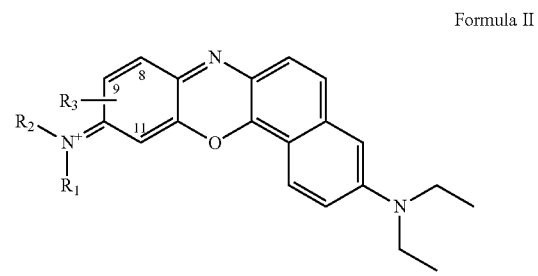

Formula II wherein $R_1$ is selected from hydrogen and $C_1$-$C_3$ alkyl;
$R_2$ is selected from hydrogen and $C_1$-$C_3$ alkyl;
$R_3$ is selected from the group of hydrogen, halogen, and $C_1$-$C_3$ alkyl;
or, when $R_3$ is bound to the 9-position carbon of the 10H-benzo[c]phenoxazine core, $R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents.

9. The compound of claim 8, of Formula II, wherein $R_1$ is hydrogen; $R_2$ is $C_1$-$C_3$ alkyl; and $R_3$ is selected from the group of hydrogen, halogen, and $C_1$-$C_3$ alkyl.

10. The compound of claim 8, of Formula II, wherein $R_1$ is hydrogen; $R_2$ is $C_1$-$C_3$ alkyl; and $R_3$ is selected from the group of hydrogen, F, Cl, and $C_1$-$C_3$ alkyl.

11. The compound of claim 8, of Formula II, wherein $R_1$ is hydrogen; $R_2$ is $C_1$-$C_2$ alkyl; and $R_3$ is selected from the group of hydrogen, F, Cl, and $C_1$-$C_2$ alkyl.

12. The compound of claim 8, of Formula II, wherein $R_1$ is selected from hydrogen and $C_1$-$C_3$ alkyl; and
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_3$ alkyl substituents.

13. The compound of claim 8, of Formula II, wherein $R_1$ is selected from hydrogen and $C_1$-$C_2$ alkyl; and
$R_2$ and $R_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 $C_1$-$C_2$ alkyl substituents.

14. The compound of claim 1, comprising Formula III:

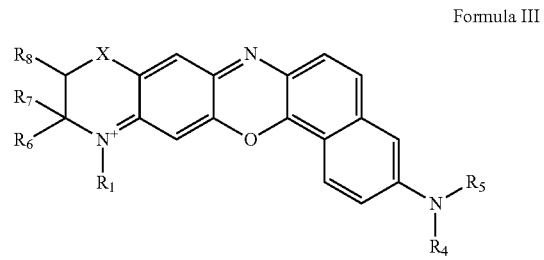

Formula III wherein R$_1$ is selected from hydrogen and C$_1$-C$_3$ alkyl;
R$_4$ and R$_5$ are each independently selected from hydrogen and C$_1$-C$_3$ alkyl;
R$_6$, R$_7$, and R$_8$ are each independently hydrogen or C$_1$-C$_3$ alkyl;
X is selected from oxygen and carbon, with carbon atom being optionally substituted by C$_1$-C$_3$ alkyl.

15. The compound of claim 14, of Formula III, wherein R$_1$ is selected from hydrogen and C$_1$-C$_2$ alkyl;
R$_4$ and R$_5$ are each independently selected from hydrogen and C$_1$-C$_2$ alkyl;
R$_6$, R$_7$, and R$_8$ are each independently hydrogen or C$_1$-C$_2$ alkyl; and
X is selected from oxygen and carbon, with carbon atom being optionally substituted by C$_1$-C$_2$ alkyl.

16. The compound of claim 14, of Formula III, wherein R$_1$ is selected from hydrogen and —CH$_3$;
R$_4$ and R$_5$ are each independently selected from hydrogen and C$_1$-C$_2$ alkyl;
R$_6$, R$_7$, and R$_8$ are each independently hydrogen or —CH$_3$; and
X is selected from oxygen and carbon, with carbon atom being optionally substituted by —CH$_3$.

17. The compound of claim 1, having the formula:

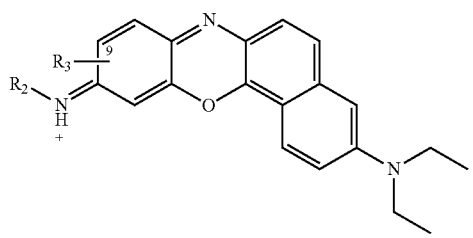

Formula IV wherein R$_3$ is methyl and R$_2$ is ethyl;
or, when R$_3$ is bound to the 9-position carbon of the 10H-benzo[c]phenoxazine core, R$_2$ and R$_3$, together with the carbon atoms to which they are bonded, form a five-membered or six-membered fused ring, the five-membered or six-membered fused ring optionally containing a ring oxygen heteroatom, and the five-membered or six-membered fused ring being substituted by 0, 1, 2, or 3 C$_1$-C$_3$ alkyl substituents.

18. The compound of claim 1, selected from the group of:

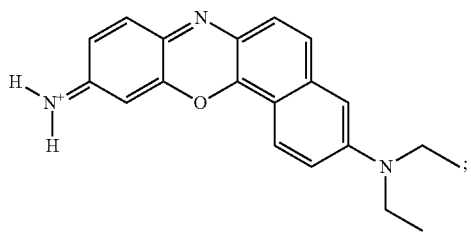

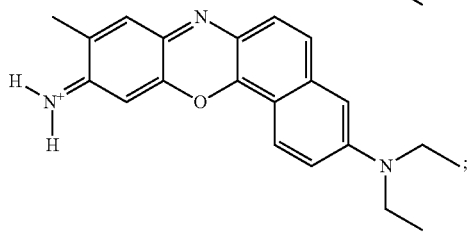

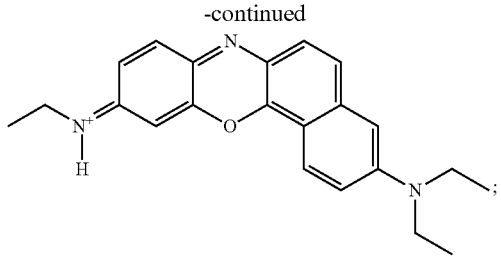

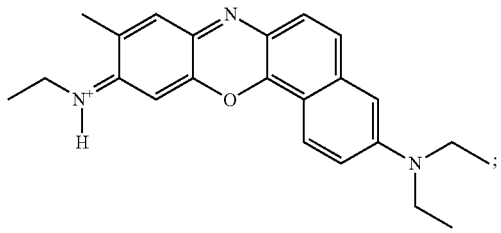

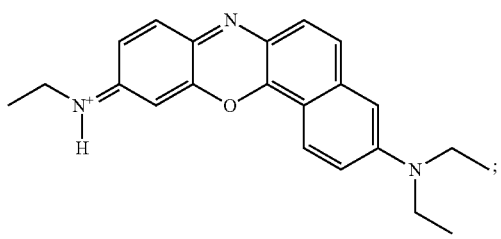

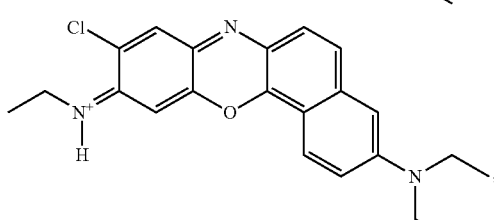

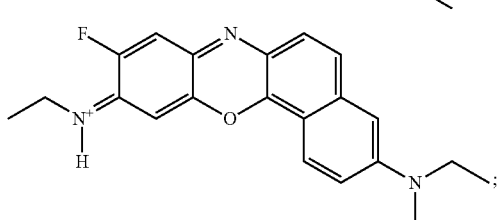

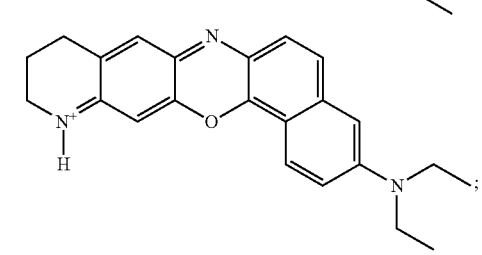

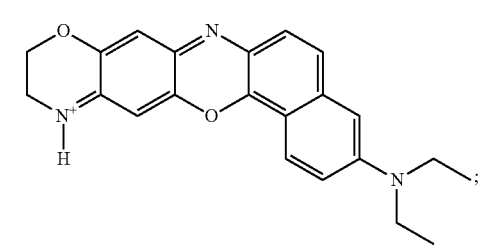

-continued
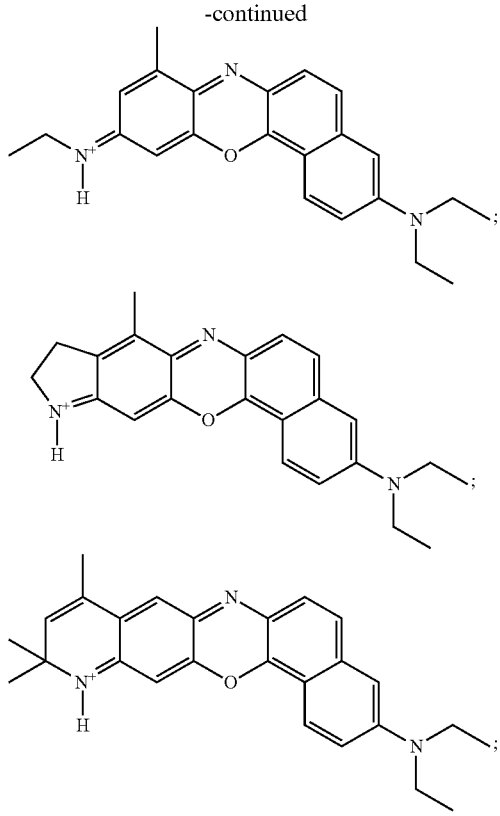
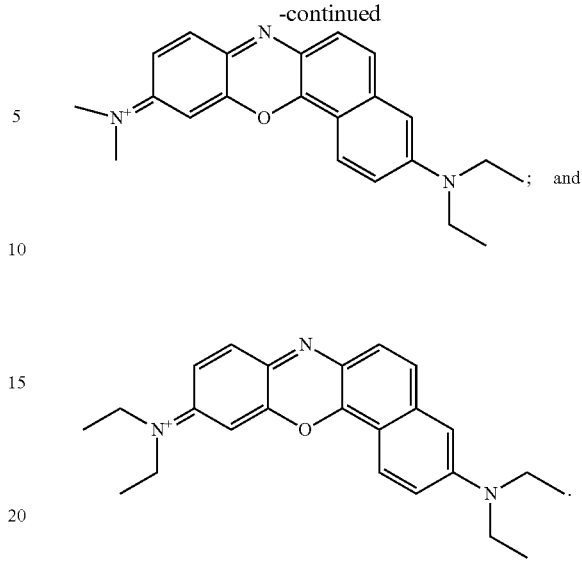
19. A composition comprising at least one compound of claim 1 and a pharmaceutically acceptable carrier or excipient.
20. A method of imaging a target area in a subject, the method comprising contacting the target area in the subject with a compound of claim 1 and detecting the compound in the target area using fluorescence or near-infrared imaging.
* * * * *